US010955322B2

(12) United States Patent
Gradinaru et al.

(10) Patent No.: US 10,955,322 B2
(45) Date of Patent: Mar. 23, 2021

(54) METHODS AND DEVICES FOR SOFT AND OSSEOUS TISSUE CLEARING AND FLUORESCENT IMAGING

(71) Applicant: California Institute of Technology, Pasadena, CA (US)

(72) Inventors: Viviana Gradinaru, La Canada-Flintridge, CA (US); Ken Y. Chan, Pasadena, CA (US); Alon Grinbaum, West Hollywood, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 15/874,673

(22) Filed: Jan. 18, 2018

(65) Prior Publication Data

US 2018/0202904 A1 Jul. 19, 2018

Related U.S. Application Data

(60) Provisional application No. 62/447,781, filed on Jan. 18, 2017.

(51) Int. Cl.
  *G01N 1/30* (2006.01)
  *G01N 1/36* (2006.01)
  (Continued)

(52) U.S. Cl.
  CPC .............. *G01N 1/30* (2013.01); *A61K 35/32* (2013.01); *G01N 1/34* (2013.01); *G01N 1/36* (2013.01);
  (Continued)

(58) Field of Classification Search
  CPC .. G01N 1/30; G01N 1/36; G01N 1/34; G01N 2001/302; G01N 2001/364; A61K 35/32
  See application file for complete search history.

(56) References Cited

U.S. PATENT DOCUMENTS

| 6,007,833 A | 12/1999 | Chudzik et al. |
|---|---|---|
| 6,232,092 B1 | 5/2001 | Rogers |

(Continued)

FOREIGN PATENT DOCUMENTS

| CN | 103169988 A | 6/2013 |
|---|---|---|
| EP | 3047271 | 7/2016 |

(Continued)

OTHER PUBLICATIONS

Extended European Search Report of EP 14845995.1 dated May 3, 2017, 9 pages.

(Continued)

*Primary Examiner* — Sean C. Barron
(74) *Attorney, Agent, or Firm* — Nixon Peabody LLP

(57) ABSTRACT

Described herein is a bone tissue clearing method with enhanced optical access. Compositions and techniques for bone tissue clearing include continuous convective flow during the clearing process, amino alcohol to minimize tissue autofluorescence, and an imaging procedure that minimizes refractive index variations in light-sheet microscopy. These improvements allowed the Inventors to achieve whole-bone clearing with an imaging depth of up to about 1.5 mm while maintaining fluorescence and a signal-to-noise ratio (SNR) that permits detection and 3D placement of single cells. In various embodiments, the present application teaches methods and kits for clearing and optionally subsequently visualizing tissue containing bone.

20 Claims, 21 Drawing Sheets

(51) Int. Cl.
A61K 35/32 (2015.01)
G01N 1/34 (2006.01)
(52) U.S. Cl.
CPC . *G01N 2001/302* (2013.01); *G01N 2001/364* (2013.01)

(56) References Cited

U.S. PATENT DOCUMENTS

| | | | |
|---|---|---|---|
| 6,465,208 | B1 | 10/2002 | Rogers |
| 6,472,216 | B1 | 10/2002 | Chiang |
| 8,399,207 | B2 | 3/2013 | Liaw et al. |
| 9,778,154 | B2 | 10/2017 | Gradinaru et al. |
| 9,778,155 | B2 | 10/2017 | Gradinaru et al. |
| 2014/0357526 | A1 | 12/2014 | Caprioli et al. |
| 2015/0087001 | A1 | 3/2015 | Gradinaru et al. |
| 2015/0144490 | A1 | 5/2015 | Diesseroth et al. |
| 2016/0123854 | A1 | 5/2016 | Gradinaru et al. |

FOREIGN PATENT DOCUMENTS

| | | |
|---|---|---|
| JP | 2003-48928 A | 2/2003 |
| JP | 2005-535752 A | 11/2005 |
| KR | 10-2016-0058900 A | 5/2016 |
| WO | 2012/161143 A1 | 11/2012 |
| WO | 2014/025392 A1 | 2/2014 |
| WO | 2015/041755 A1 | 3/2015 |
| WO | 2016/073941 A1 | 5/2016 |
| WO | 2017/031249 A1 | 2/2017 |

OTHER PUBLICATIONS

International Search Report and Written Opinion for PCT/US2014/048985 dated Nov. 25, 2014, 12 pages.
International Preliminary Report on Patentability for PCT/US2014/048985 dated Mar. 22, 2016, 8 pages.
International Search Report and Written Opinion for PCT/US2015/059600 dated May 12, 2016, 6 pages.
International Preliminary Report on Patentability for PCT/US2015/059600 dated May 9, 2017, 5 pages.
International Search Report and Written Opinion for PCT/US2016/047430 dated Nov. 22, 2016, 12 pages.
Albrecht et al., Photo- and Electropatterning of Hydrogel-Encapsulated Living Cell Arrays., Lab on a Chip, 2005, vol. 5(1), pp. 111-118.
Brede et al., Mapping Immune Processes in Intact Tissues at Cellular Resolution, The Journal of Clinical Investigation, 2012, vol. 122(12), pp. 4439-4446.
Chung et al., Structural and Molecular Interrogation of Intact Biological Systems, Nature, 2013, vol. 497, pp. 332-339.
Erturk et al., Three-Dimensional Imaging of the Unsectioned Adult Spinal Cord to Assess Axon Regeneration and Glial Response after Injury, Nature Medicine, 2012, vol. 18(1), pp. 166-171.
Genina et al. Optical Clearing of Cranial Bone. Advances in Optical Technologies (2008); 9 pages.
Greenberg et al., Perilipin, a Major Hormonally Regulated Adipocyte-specific Phosphoprotein Associated with the Peripehery of Lipid Storage Droplets, The Journal of Biological Chemistry, 1991, vol. 266(17), pp. 11341-11346.
Hoffman, A.S., Hydrogels for Biomedical Applications, Advanced Drug Delivery Reviews, 2002, vol. 54, pp. 3-12.
Kiviranta et al. The Rate of Calcium Extraction During EDTA Decalcification from Thin Bone Slices as Assessed with Atomic Absorption Spectrophotometry. Histochemistry (1980). 68:119-127.
Leica HCX PL APO 63X/1.3 GLYC CORR CS (21(degrees)C). Leica technical bulletin for glycerol microscope objectives. (2004) 8 pages.
Lu et al. Modeling of Two-Phase Polymerization of Acrylamide in Aqueous Poly(ethylene Glycol) Solution, AIChE Journal, 2011, vol. 57(9), pp. 2493-2504.
Lund et al. Lipid composition of normal human bone marrow as determined by column chromatography. Journal of Lipid Research (1962). 3(1):95-98.
O'Brien et al. Lipid composition of the normal human brain: gray matter, white matter, and myelin. Journal of Lipid Research (1965). 6:537-544.
Oosthuysen et al., Bioprosthetic Tissue Preservation by Filling with a Poly(acrylamide) Hydrogel, Biomaterials, 2006, vol. 27(9), pp. 2123-2130.
Ott et al., Perfusion-Decellularized Matrix: Using Natures Platform to Engineer a Bioarticial Heart, Nature Medicine, 2008, vol. 14(2), pp. 213-221.
Tainaka et al. Whole-Body Imaging with Single-Cell Resolution by Tissue Decoloization. Cell (2014). 159:911-924.
Tomer et al., Advanced Clarity for Rapid and High-Resolution Imaging of Intact Tissues., Nat Protoc, 2014, vol. 9 (7), pp. 1682-1697.
Treweek et al. Whole-body tissue stabilization and selective extractions via tissue-hydrogel hybrids for high-resolution intact circuit mapping and phenotyping. Nat Protoc (2015). 10(11)1860-1896.
Wang et al. Long-term outcome of cryopreserved bone-derived osteoblasts for bone regeneration in vivo. Biomaterials (2011). 32:4546-4555.
Washington et al., Frontal Polymerization Synthesis of Temperature-Sensitive Hydrogels., J. Am. Chem., 2001, vol. 123(32), pp. 7933-7934.
Yang et al. Single-Cell Phenotyping within Transparent Intact Tissue Through Whole-Body Clearing. Cell (2014). 158 (4):945-958.

Figure 2
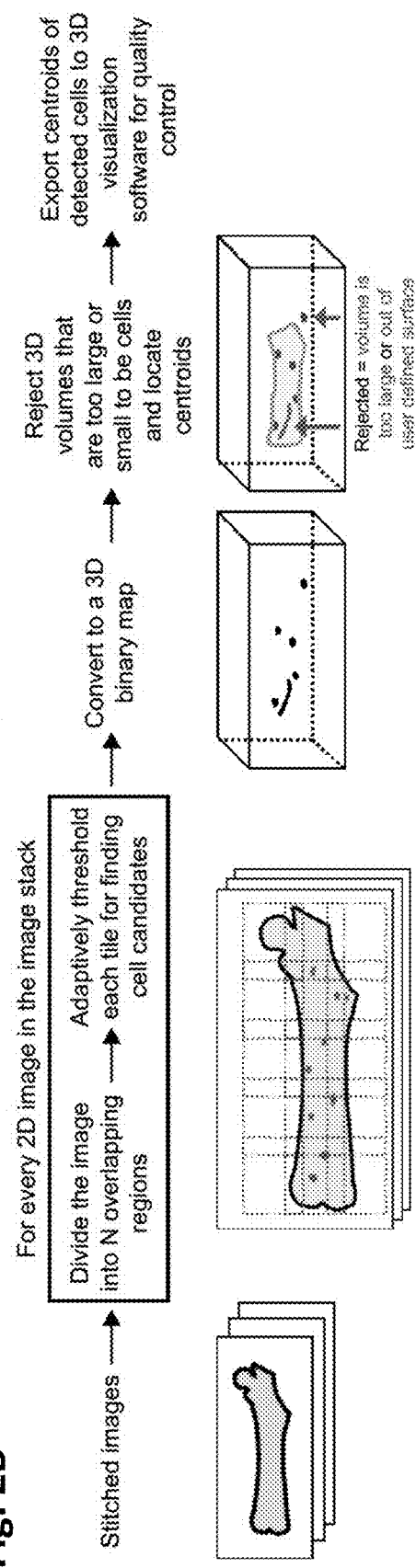
Fig. 2B
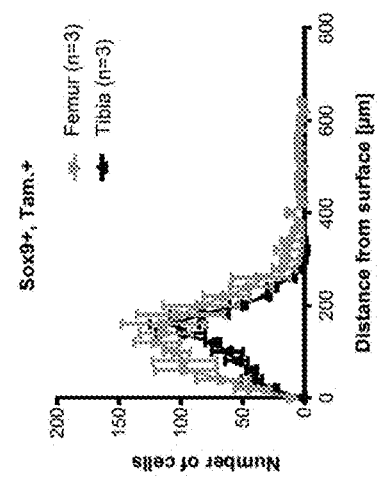
Fig. 2D
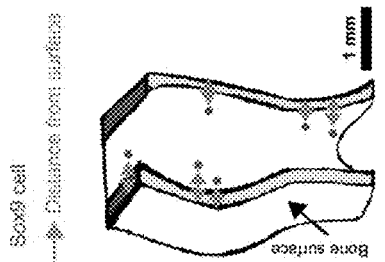
Fig. 2E
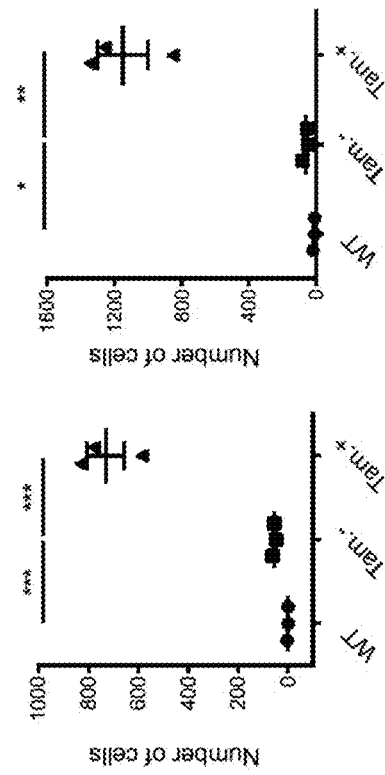
Fig. 2C

Figure 3
Fig. 3A
Tranverse cut
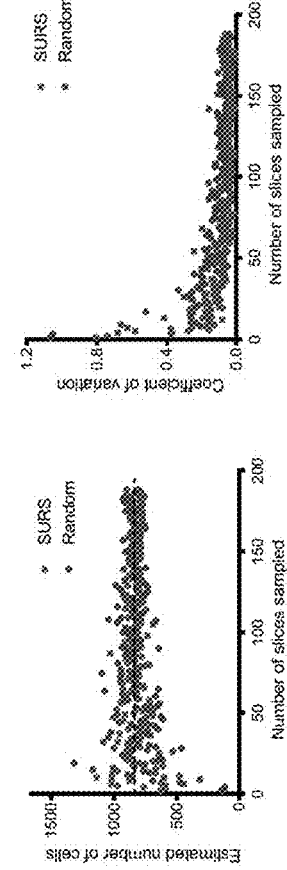
Femur
Tibia
Vertebral body
Fig. 3B
Simulated stereology experiment of 6 μm slices
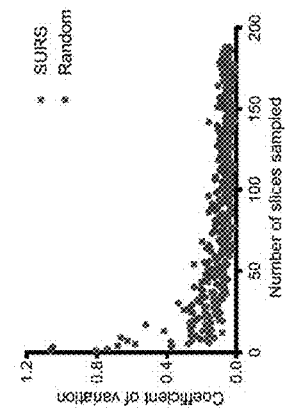
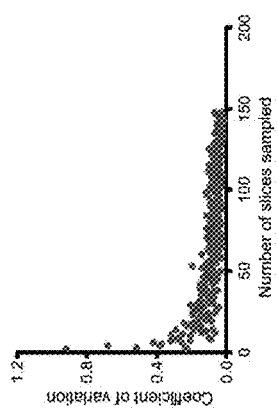
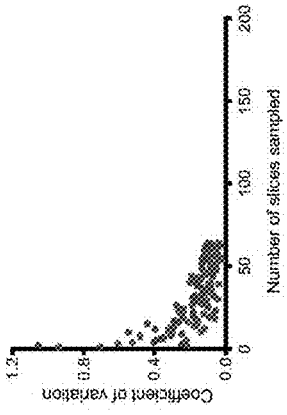
Fig. 3C
Coefficient of variation across multiple experiments
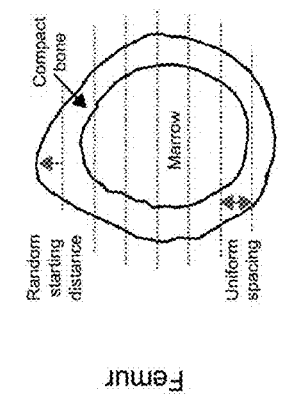
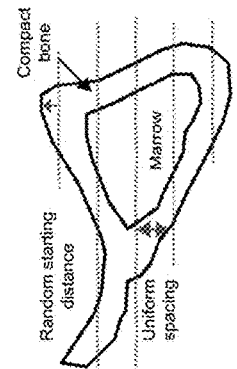
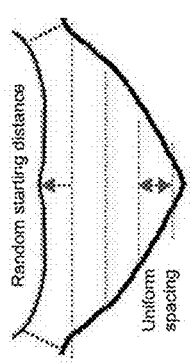

Figure 4
Fig. 4A
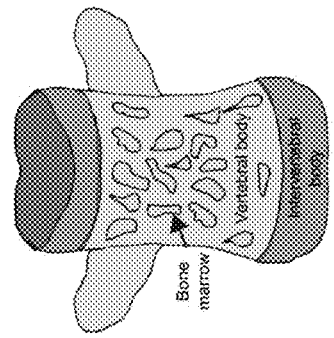
Fig. 4B
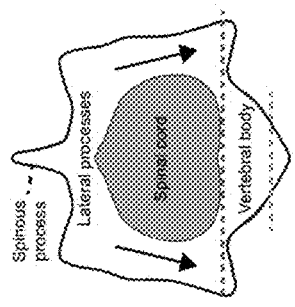
Fig. 4C
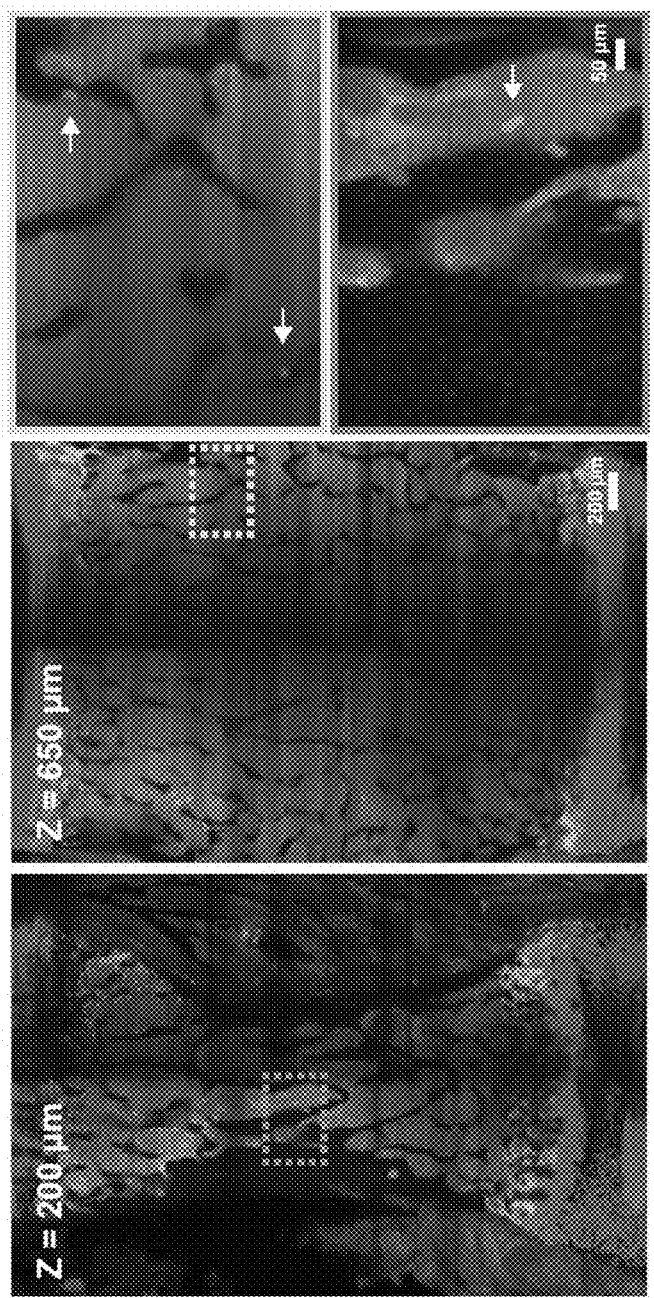

Figure 4
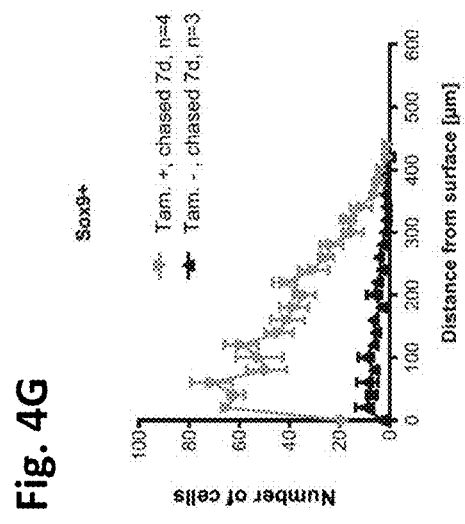
Fig. 4D
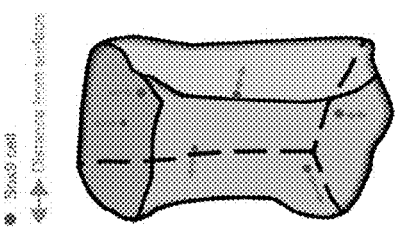
Fig. 4E
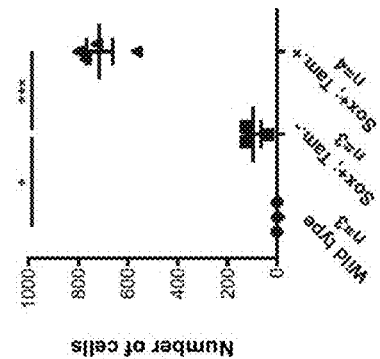
Fig. 4F
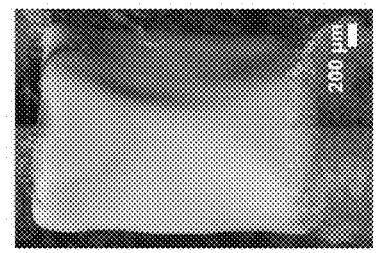
Fig. 4H
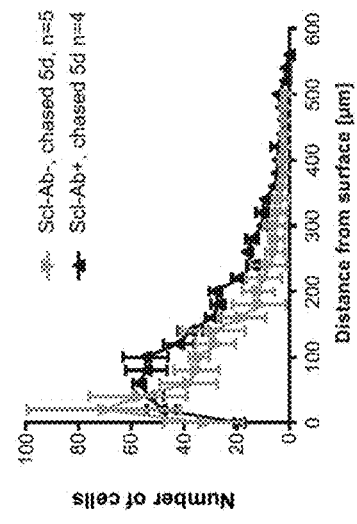
Fig. 4G
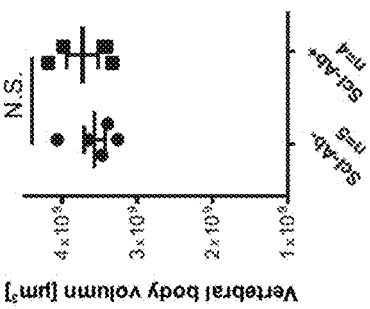
Fig. 4I
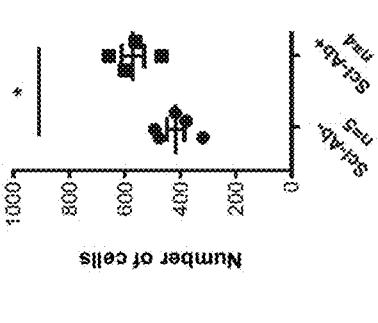
Fig. 4J
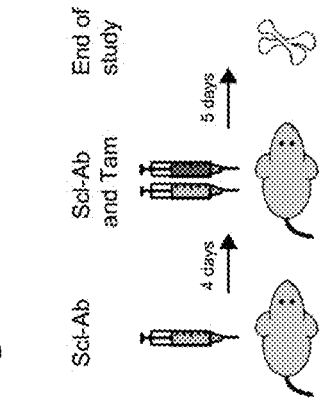
Fig. 4K

Figure 6
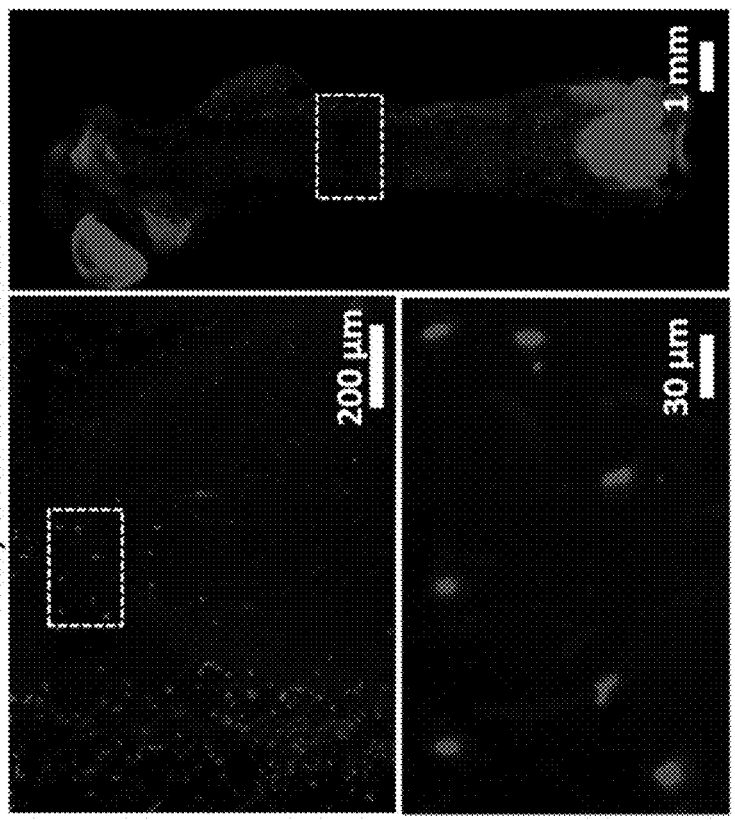
Fig. 6A
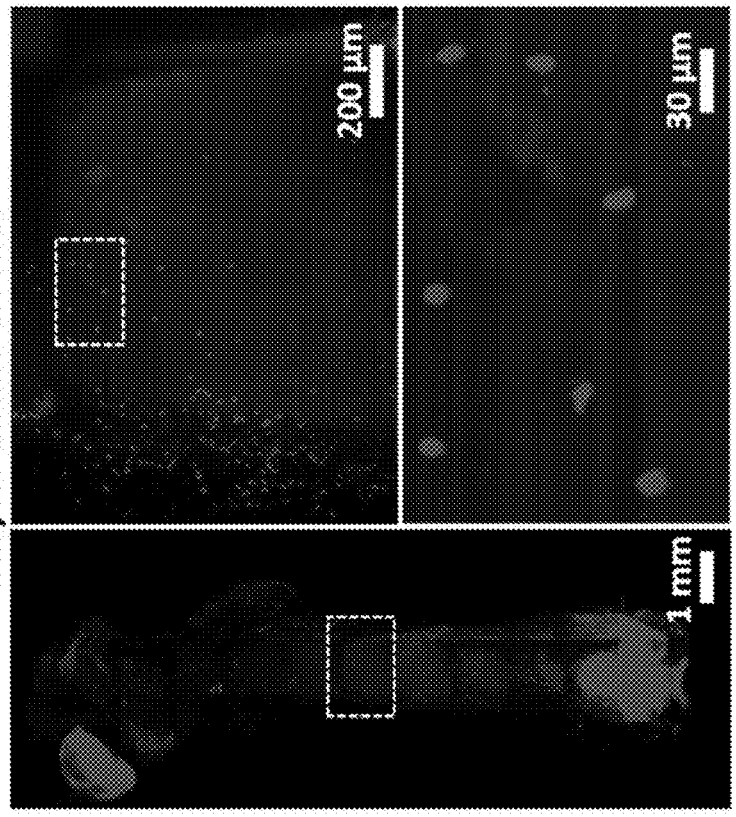
Fig. 6B

Figure 6
Fig. 6C
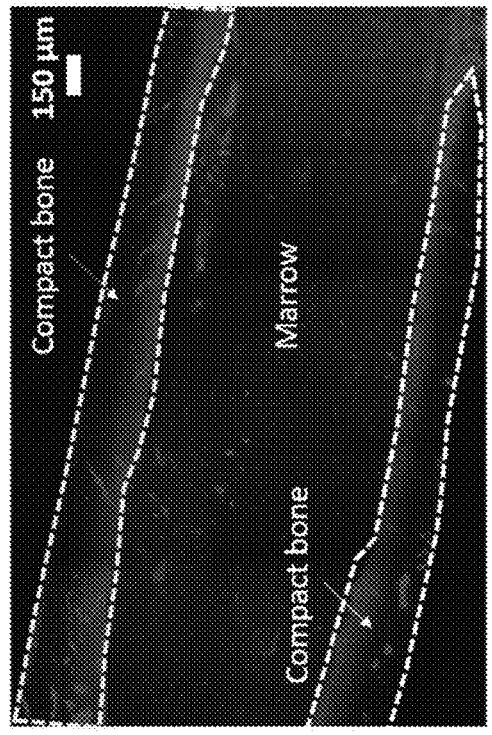
Fig. 6D
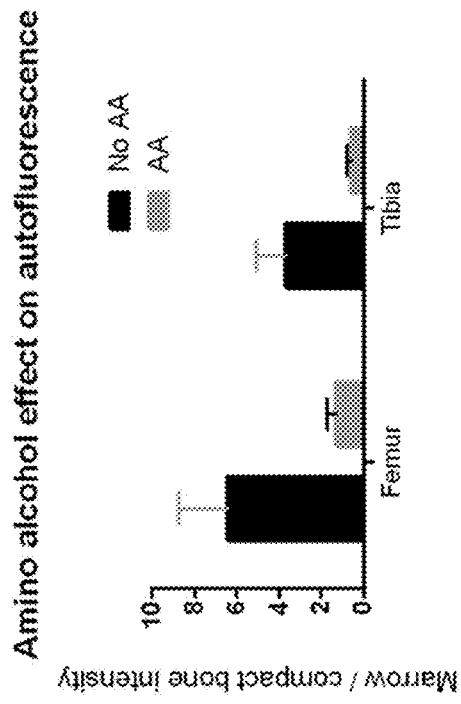
Fig. 6E
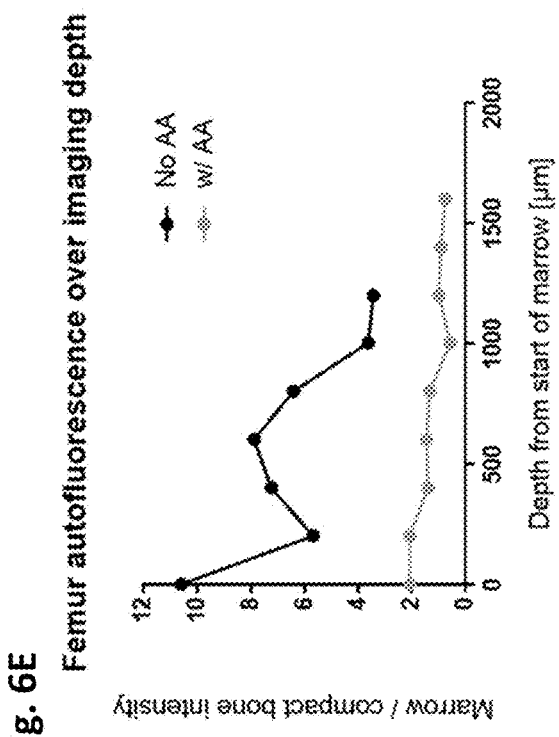

Figure 7
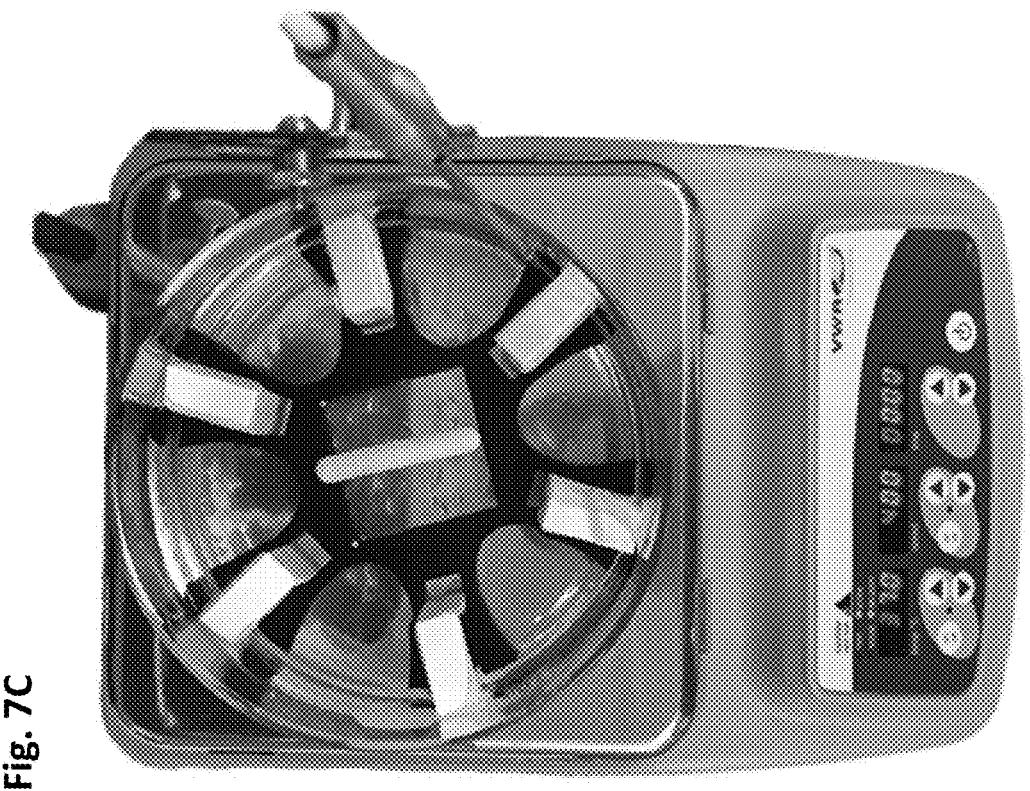
Fig. 7C
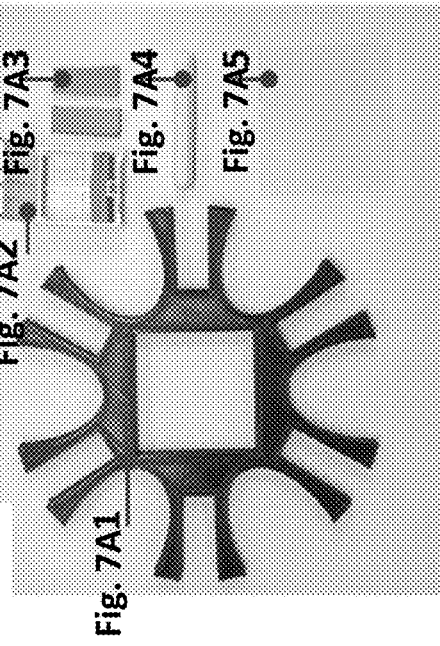
Fig. 7A
Fig. 7A1, Fig. 7A2, Fig. 7A3, Fig. 7A4, Fig. 7A5
Fig. 7B

Figure 8
Fig. 8A
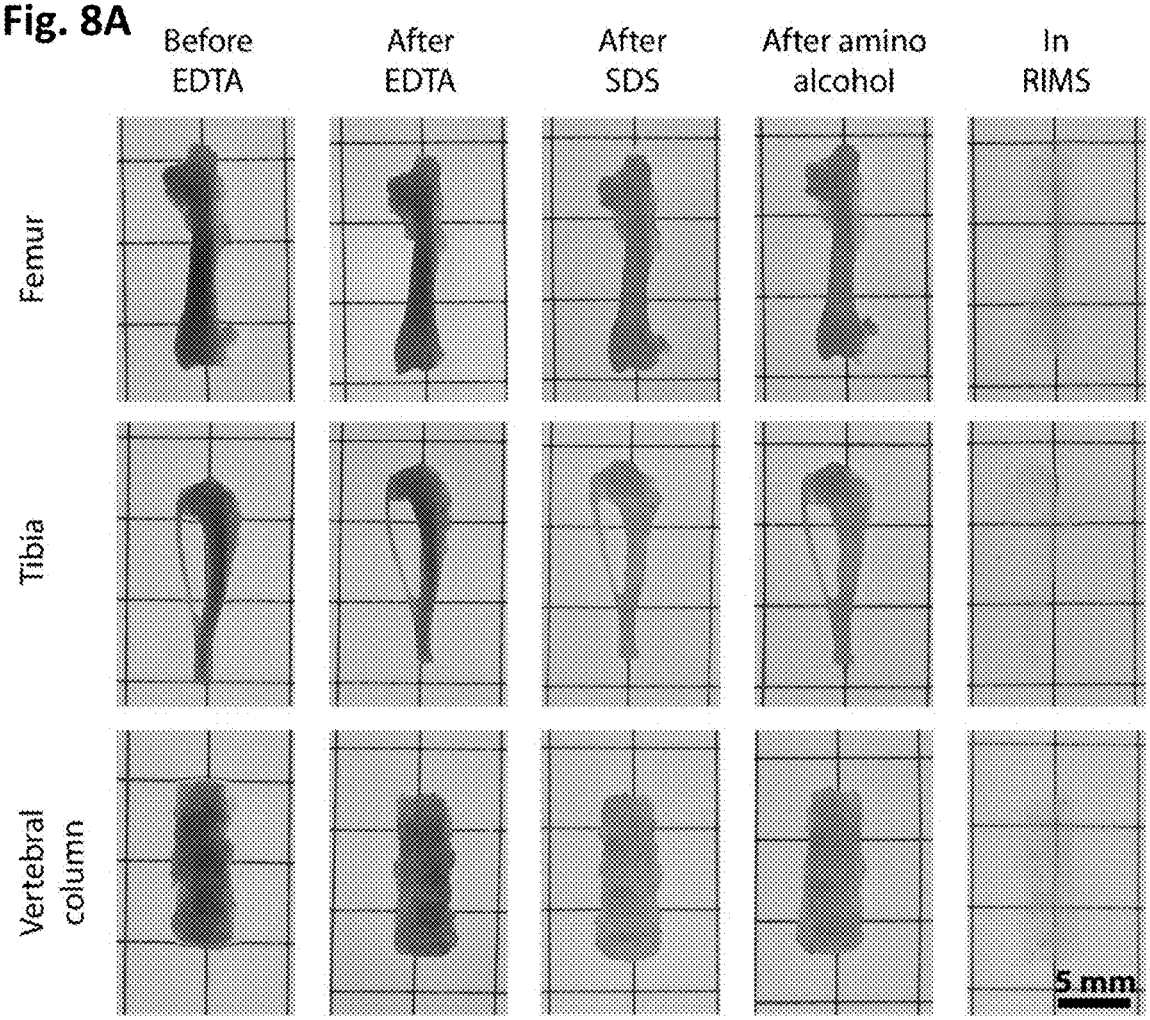
Fig. 8B
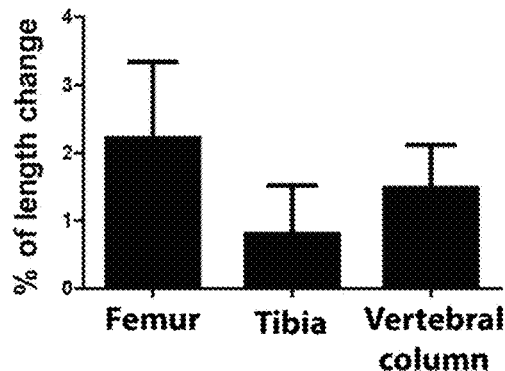
Fig. 8C
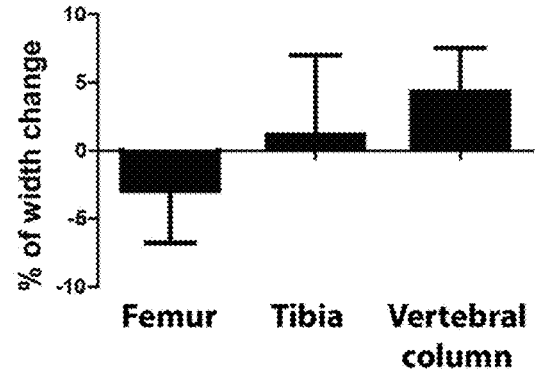

Figure 9
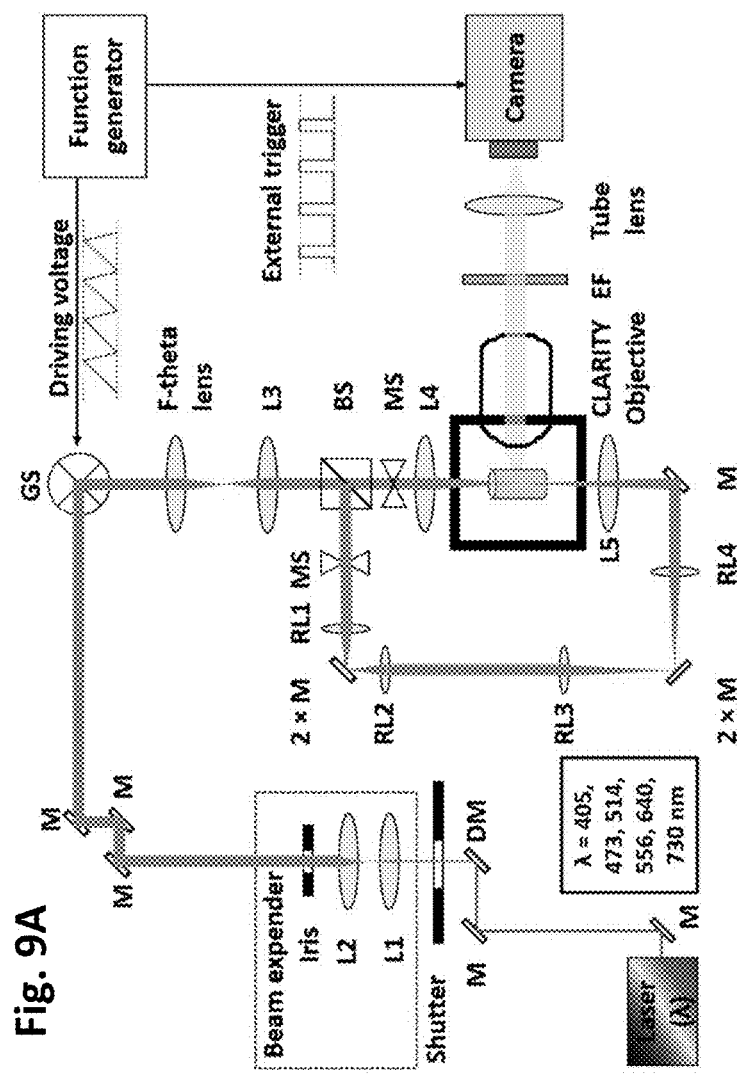
Fig. 9A
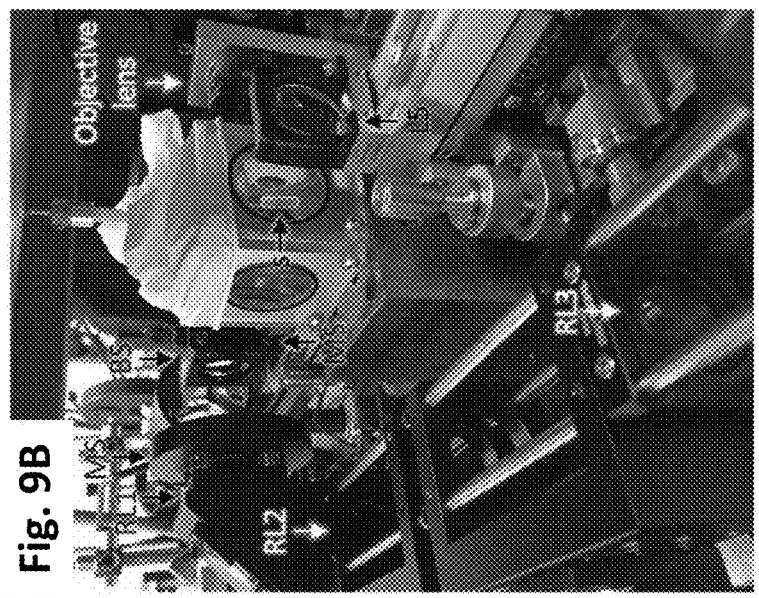
Fig. 9B

Figure 10
Fig. 10A
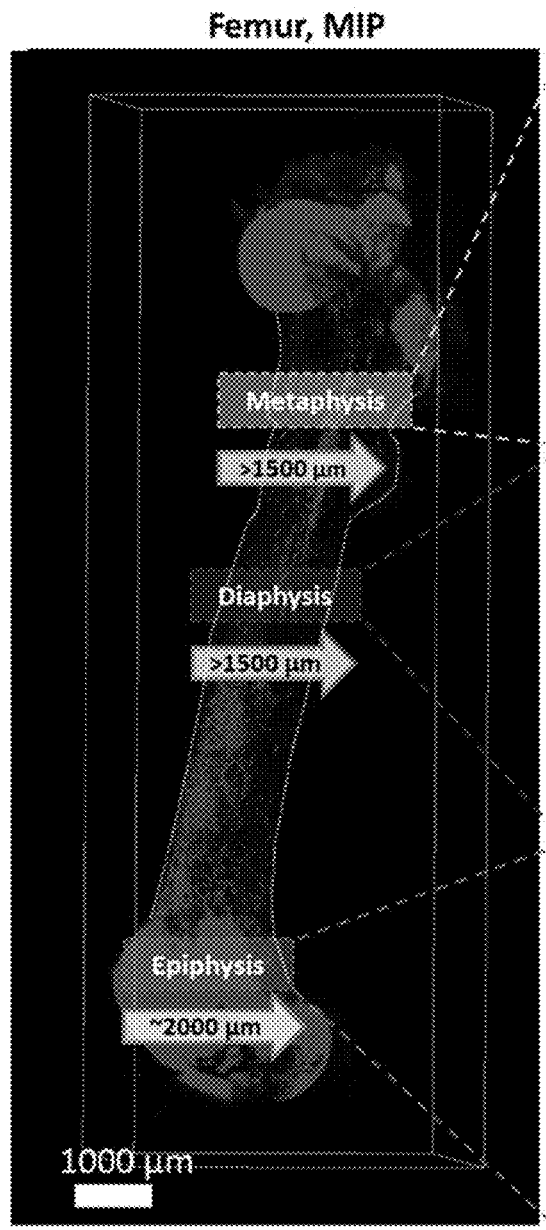
Fig. 10B
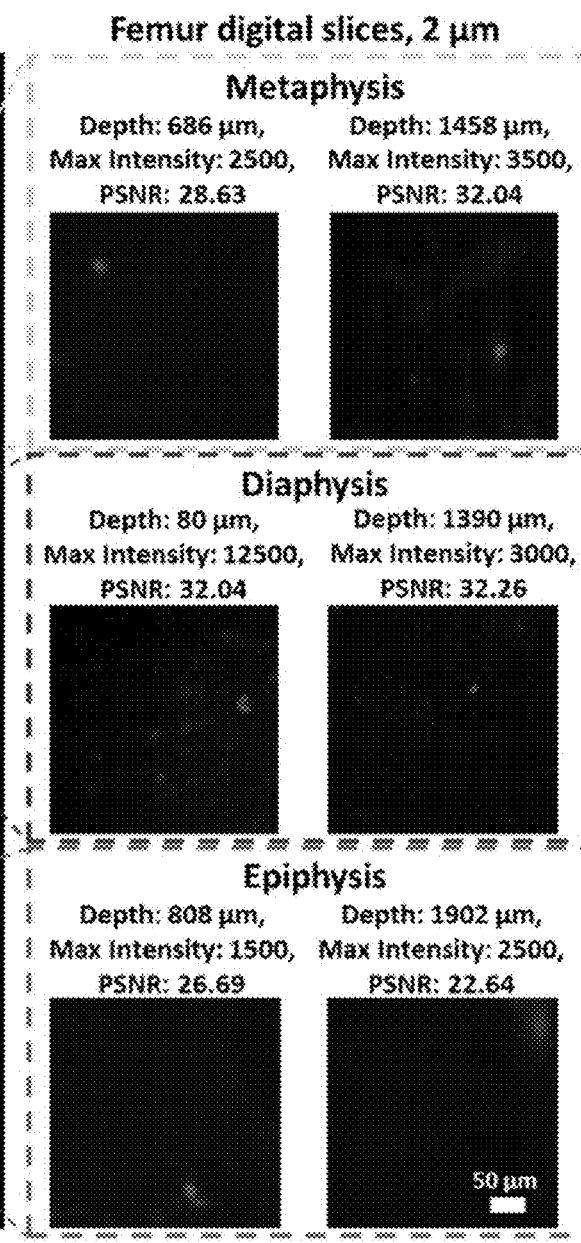

Figure 10
Fig. 10C
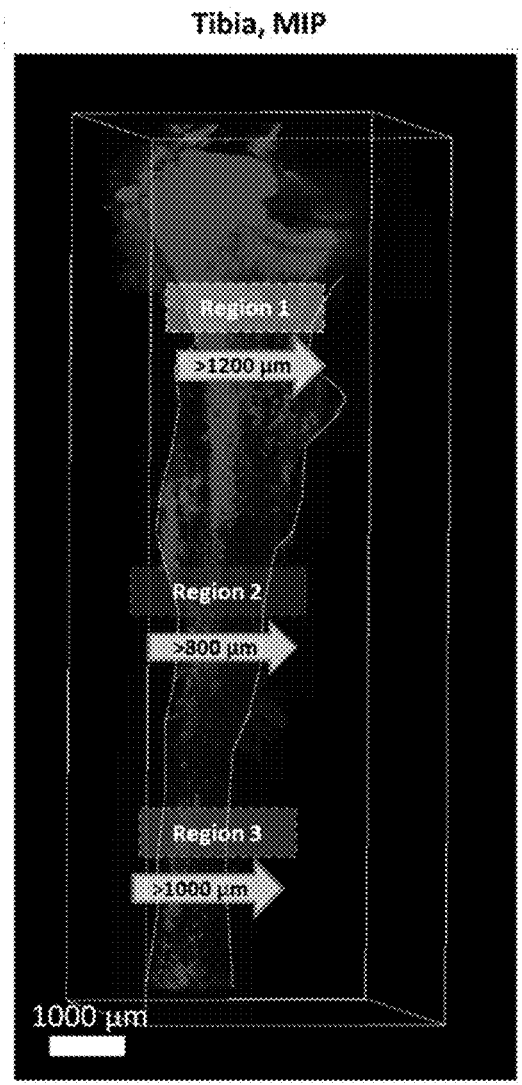
Fig. 10D
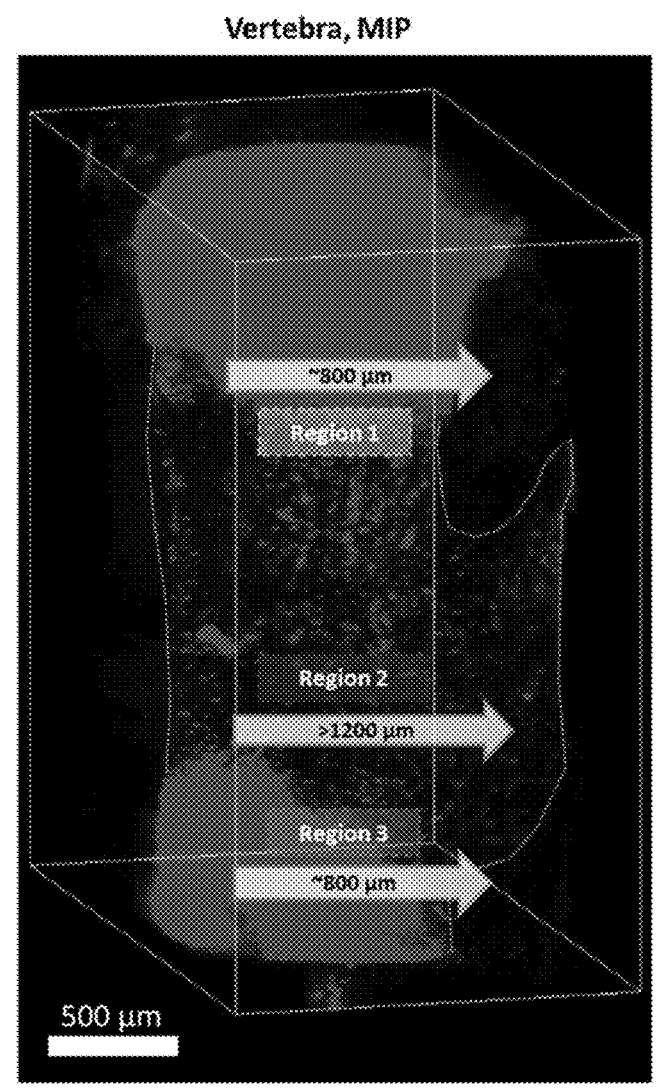

Figure 10
Fig. 10E
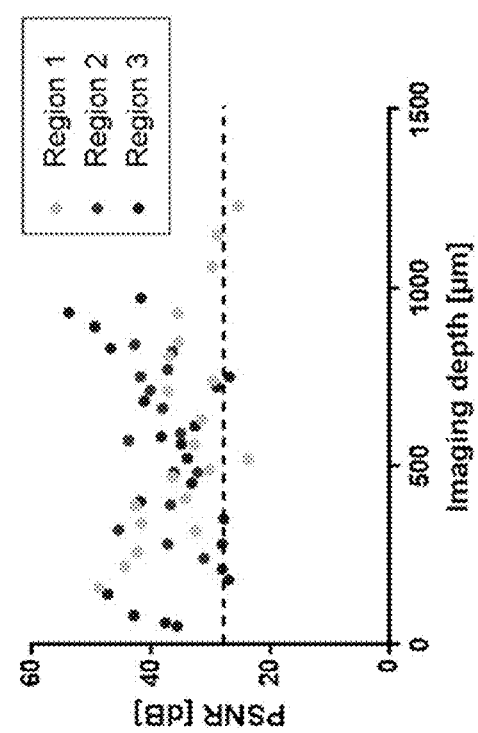
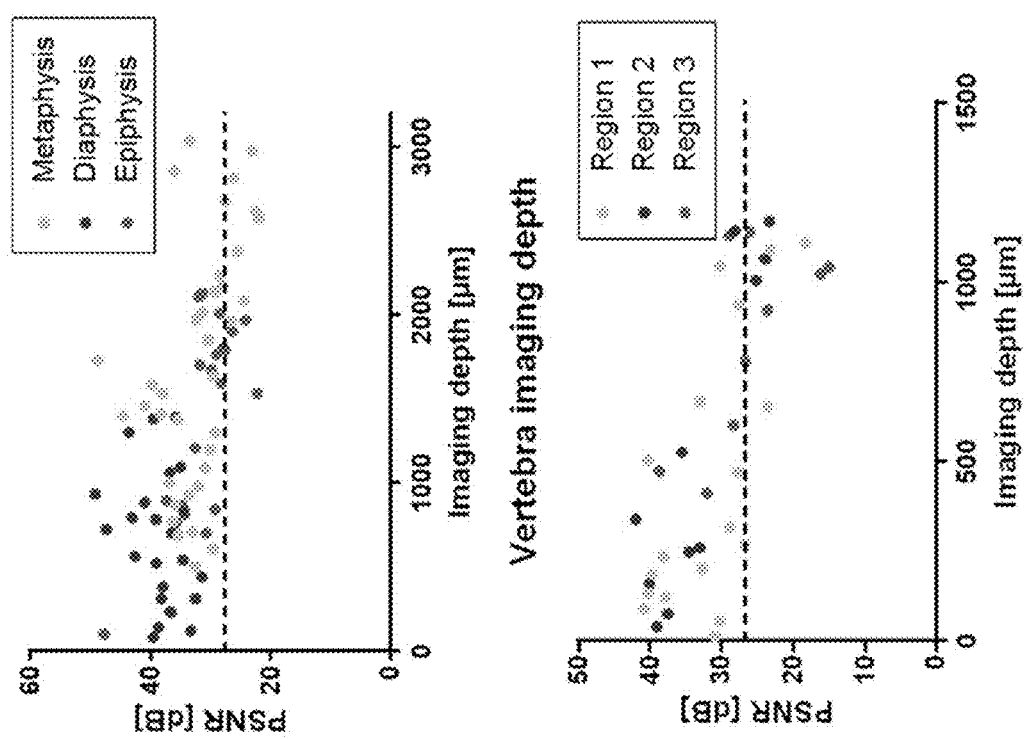
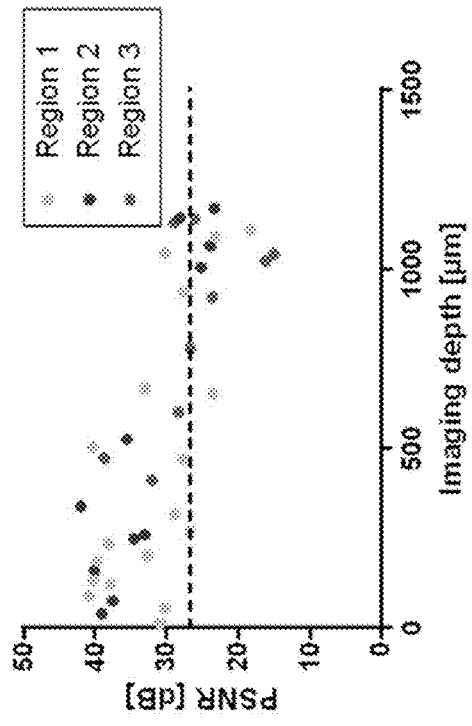

Femur

Tibia

METHODS AND DEVICES FOR SOFT AND OSSEOUS TISSUE CLEARING AND FLUORESCENT IMAGING

CROSS-REFERENCE TO RELATED APPLICATION

This application also claims the benefit of priority under 35 U.S.C. § 119(e) to U.S. Provisional Patent Application No. 62/447,781 filed on Jan. 18, 2017. The contents of all of the aforementioned applications are hereby incorporated herein by reference in their entirety.

GOVERNMENT RIGHTS

This invention was made with government support under Grant No. OD017782 awarded by the National Institutes of Health. The government has certain rights in the invention.

FIELD OF THE INVENTION

The present invention generally relates to the field of tissue preparation and characterization.

BACKGROUND

Bone tissue harbors unique and essential physiological processes, such as hematopoiesis, bone growth, and bone remodeling. Due to its calcified nature, most mammalian osseous tissue does not afford easy access to three-dimensional information. Visual representations of the spatial distribution and properties of cells within a bone sample must be obtained via the sectioning, labeling and imaging of thin tissue slices, and the reconstruction of these digital image datasets. Bone-sectioning, however is both physically challenging given the hard, fibrous nature of osseous tissue, and risks incurring extensive damage to the tissue sample. Thus, there is a great need in the art to develop compositions and techniques for visualizing cellular morphology, tissue architecture, macromolecular/cellular content, and biomolecule/protein antigenicity that biological, immunological, and 3D structural properties of osseous tissues may be studied in healthy and diseased state.

To enable visualization of these processes at the cellular level in an intact environment, the Inventors developed a bone tissue clearing method with enhanced optical access. The Inventors discovered that decalcification of bones by EDTA could aid in visualization of osseous tissues.

Described herein is a specialized protocol that incorporates continuous convective flow during the clearing process, amino alcohol to minimize tissue autofluorescence, and an imaging procedure that minimizes RI variations in light-sheet microscopy. These improvements allowed the Inventors to achieve whole-bone clearing with an imaging depth of up to about 1.5 mm while maintaining fluorescence and a signal-to-noise ratio (SNR) that permits detection and 3D placement of single cells.

SUMMARY OF THE INVENTION

Described herein is a method, including fixing a bone tissue sample by applying a fixative solution to generate a fixed bone tissue sample, decalcifying the fixed bone tissue sample by applying a decalcifying solution including a calcium chelating agent to generate a decalcified bone tissue sample, stabilizing the decalcified bone tissue sample by applying a hydrogel monomer solution, initiating polymerization of the monomer solution to generate a decalcified bone tissue sample hydrogel matrix, washing the decalcified bone tissue sample hydrogel matrix, removing lipids from the washed decalcified bone tissue sample hydrogel matrix by applying a detergent solution to generate a substantially cleared bone tissue sample, removing heme from the substantially cleared bone tissue sample by applying a removal solution including an amino alcohol to generate a cleared bone tissue sample, and further washing the cleared bone tissue sample. In other embodiments, the fixative solution includes 2-6% paraformaldehyde (PFA). In other embodiments, the fixative solution includes 4% PFA. In other embodiments, the calcium chelating agent includes ethylenediaminetetraacetic acid (EDTA). In other embodiments, the hydrogel monomer solution includes 2-8% acrylamide. In other embodiments, the hydrogel monomer solution includes 4% acrylamide. In other embodiments, the method includes placing the decalcified bone tissue sample into a substantially air tight chamber, and introducing nitrogen into the substantially air tight chamber. In other embodiments, the hydrogel monomer solution includes a thermoinitiator or photoinitiator. In other embodiments, the detergent solution includes 6-15% sodium dodecyl sulfate (SDS). In other embodiments, the detergent solution includes 8% SDS. In other embodiments, the removal solution including the amino alcohol includes N,N,N',N'-Tetrakis(2-Hydroxypropyl)ethylenediamine. In other embodiments, the removal solution includes 25% N,N,N',N'-Tetrakis(2-Hydroxypropyl)ethylenediamine. In other embodiments, the method includes serially applying refractive index matching solutions (RIMS) with progressively higher refractive indexes (RIs) to the cleared bone tissue sample. In other embodiments, a first RIMS in which the tissue including the bone of the subject is incubated has an RI of 1.36-1.40. In other embodiments, a second RIMS in which the tissue including bone is incubated has an RI of 1.41-1.45. In other embodiments, a third RIMS that has an RI of 1.45-1.47. In other embodiments, the stirring, flow assistance or constant flow is introduced for one or more steps of: applying a decalcifying solution, applying a hydrogel monomer solution, washing the decalcified bone tissue sample hydrogel matrix, applying a detergent solution to generate a substantially cleared bone tissue sample, applying a removal solution, and further washing the cleared bone tissue sample. In other embodiments, the method includes using a microscope to visualize the tissue including the bone of the subject that has been incubated in the final RIMS. In other embodiments, the microscope is a light sheet microscope. In other embodiments, the bone tissue sample is excised from a host organism subject to perfusion, including perfusion with PFA.

Further described herein is a method including fixing a bone tissue sample by applying a fixative solution including 4% paraformaldehyde (PFA) to generate a fixed bone tissue sample, decalcifying a fixed bone tissue sample by applying a decalcifying solution including ethylenediaminetetraacetic acid (EDTA) and stirring to generate a decalcified bone tissue sample, stabilizing the decalcified bone tissue sample by applying a hydrogel monomer solution including 4% acrylamide with flow assistance, initiating polymerization of the monomer solution to generate a decalcified bone tissue sample hydrogel matrix, washing the decalcified bone tissue sample hydrogel matrix with flow assistance, removing lipids from the washed decalcified bone tissue sample hydrogel matrix by applying a detergent solution including 8% sodium dodecyl sulfate (SDS) with flow assistance to generate a substantially cleared bone tissue sample, removing heme from the substantially cleared bone tissue sample by applying a removal solution including 25% N,N,N',N'-Tetrakis(2-Hydroxypropyl)ethylenediamine with flow assistance to generate a cleared bone tissue sample, and further washing the cleared bone tissue sample with constant stirring.

BRIEF DESCRIPTION OF THE FIGURES

(FIG. 1A) Micrographs of mouse tibia, femur, and vertebral column before and after CLARITY. Bones were rendered transparent using Bone CLARITY. (FIG. 1B) Block diagram outlining of the key steps of Bone CLARITY sample preparation. The procedure includes the following: demineralization, hydrogel stabilization, lipid removal via constant flow, and autofluorescence removal. (FIG. 1C) A schematic diagram of the imaging and computational pipeline that uses the interface between 3D visualization and image-processing programs.

(FIG. 2B) Block diagram of the semiautomated cell detection pipeline where cell candidates are identified via adaptive thresholding and their volume calculated. A predetermined selection criterion based on cell volume is used to reject blood vessels or any detected blobs that are too large or too small. (FIG. 2C) A comparison of fluorescently labeled $Sox9^+$ cell numbers between the experimental group [tamoxifen-positive ($Tam^+$)] and control groups [wild-type (WT) and tamoxifen-negative ($Tam^-$)] for the femur and tibia. n=3 animals per group; 1 bone per animal. For tibia: WT versus $Sox9^+;Tam^-$, P=0.0002 and $Sox9^+;Tam^-$ versus $Sox9^+;Tam^+$, P=0.0008. For femur: WT versus $Sox9^+;Tam^-$, P=0.012 and $Sox9^+;Tam^-$ versus $Sox9^+;Tam^+$, P=0.002. All values are means±SEM; two-tailed, unpaired t test. (FIG. 2D) Schematic showing how the distance of Sox9 cells from the surface is calculated. (FIG. 2E) The distribution of the number of $Sox9^+$ cells versus the distance from the bone surface. All values are means±SEM represent the boundaries of the compact bone. MIP fluorescence image of the vertebral body.

FIG. 3. Using intact tissue clearing methods reduces cell estimate variability compared with traditional tissue sectioning methods. (FIG. 3A) Schematic diagram showing the sample selection procedure for systematic uniform random sampling (SURS) of the mouse femur, tibia, and vertebral body. n uniformly spaced 2D sections are selected, offset by a random starting distance. The red single arrow indicates the random starting point, whereas the double arrow indicates the distance between the 2D sections. (FIG. 3B) $Sox9^+$ cell number estimation as a function of the number of sampled sections in a representative simulated stereology experiment using both SURS (red dots) and simple random sampling (blue dots). To simulate a stereology experiment, the Inventors used the cell density in the sampled sections to interpolate the cell number in the entire VOI. The black dashed line represents the ground truth, cell number based on the entire volume. (FIG. 3C) The coefficient of variation of five simulated stereology cell number estimates as a function of the number of sampled slices using SURS (red dots) and simple random sampling (blue dots).

FIG. 4. Bone CLARITY enables quantification of the effect of Scl-Ab on the number of fluorescently labeled Sox9 cells in the mouse vertebra. (FIG. 4A) Schematic depicting the lateral view of a mouse vertebra. The intervertebral disc is labeled in red; chondrocytes proliferate there after differentiation from $tdTomato-Sox9^+$ cells (chased for 7 days). The marrow is represented in light orange. (FIG. 4B) Transverse view of an L4 vertebra. The cell counts are isolated to the vertebral body, and the dashed lines approximate the locations of the sections shown in (FIG. 4C). (FIG. 4C) Digital sections (30 mm thick) at different depths along the vertebral body (Z=200 and 650 mm) (red, Sox9; and green, autofluorescence). The intervertebral discs are notable at the vertical boundaries of the images. The white arrows in the color-coded magnified images point to Sox9 cells, and the dashed white line in the magnified image marks the interface between the compact bone and the marrow. (FIG. 4D) Micrograph of the mouse vertebral body showing a representative VOI (gray surface), which does not include the intervertebral discs. (FIG. 4E) Total cell number in tamoxifen-injected mice versus control groups. For WT versus $Sox9^+;Tam^-$, P=0.0311 and $Sox9^+;Tam^-$ versus $Sox9^+;Tam^+$, P=0.0002. (FIG. 4F) Schematic showing how cell distance from surface is determined on a transparent vertebral body VOI. For each cell, the distance is defined as the shortest path to the surface in any direction. (FIG. 4G) The distribution of $Sox9^+$ cells as a function of distance from the endocortical surface. (FIG. 4H) Schematic of the Scl-Ab experimental timeline. (FIG. 4I) Quantification of the number of cells within the VOI in the Scl-Ab and vehicle-treated mice. For $Sox9^+;Tam^+;Scl-Ab^-$ versus $Sox9^+;Tam^+;Scl-Ab^+$, P=0.0183. (FIG. 4J) No significant change in the vertebral body volume was observed between the Scl-Ab group and the vehicle group. For $Sox9^+;Tam^+;Scl-Ab^-$ versus $Sox9^+;Tam^+;Scl-Ab^+$, P=0.3403. (FIG. 4K) The distribution of $Sox9^+$ cells as a function of distance from the endocortical surface. All values are means±SEM; two-tailed, unpaired t test.

FIG. 6. The effect of amino alcohol on reducing auto-fluorescence. (FIG. 6A) MIP of a mouse femur rendered transparent using Bone CLARITY without the addition of amino alcohol. The dashed regions show the locations of progressively zoomed in images. (FIG. 6B) MIP of the same mouse femur shown in (FIG. 6A), after the addition of amino alcohol. Zoomed in images of the same regions as in (FIG. 6A) show that the same spatial pattern in the sample was maintained after amino alcohol treatment. (FIG. 6C) A representative image of the regions of tissue (marrow and compact bone) used for the analysis of the auto-fluorescence quenching effect. (FIG. 6D) The mean ratio of marrow to compact bone intensity in a mouse femur and tibia before and after the addition of amino alcohol—which removes auto-fluorescence in the bone marrow. The intensity ratio between the marrow and compact bone should be independent of the imaging depth and illumination variations. (FIG. 6E) The ratio of marrow to compact bone intensity from different sample regions along the imaging depth of the bone. A depth of 0 µm refers to the first region along the imaging depth that had both marrow and compact bone.

FIG. 7. The Bone CLARITY flow chamber. (FIG. 7A) The flow chamber is composed of: (FIG. 7A1) A 3D printed holder for histology cassettes. (FIG. 7A2) A large histology cassette with rubber inserts. (FIG. 7A3) Rubber inserts to prop the tissue above the 3D printed holder, and consequently position the tissue within the convective current. (FIG. 7A4) A stir bar. (FIG. 7A5) A glass slide for placement of the stir bar above the 3D printed holder. (FIG. 7B) An assembled flow chamber inside a 15 cm petri dish with a 14.7 cm plastic petri dish cover. (FIG. 7C) The flow chamber on a closed loop temperature controlled stir plate. For repeatability, six cassettes are always placed in the chamber, and the stir bar is rotated at a speed of 400 rotations per minute at 37° C.

FIG. 8. Sample progression through Bone CLARITY clearing process. (FIG. 8A) The progression of the femur, tibia and vertebral column throughout each phase of Bone CLARITY. (FIG. 8B) The percent change in length of the bones before and after Bone CLARITY. (FIG. 8C) The percent change in width of the bones before and after Bone CLARITY. For (FIG. 8B) and (FIG. 8C), n=6 for the femur, n=5 for the tibia and n=4 for the vertebral column. All values are mean±s.e.m.

FIG. 9. LSFM set-up. (FIG. 9A) Schematic diagram of the multi-color dual-side illumination light-sheet microscope with the confocal slit detection. The microscope acquisition speed is up to 50 frames per second; consequently, it allows for high-resolution acquisition of large cleared tissue. L—lens, M—mirror, DM—dichroic mirror, GS—galvano scanner, BS—beam splitter, MS—mechanical shutter, RL—relay lenses and EF emission filter. (FIG. 9B) A photograph of the light-sheet setup, the sample is directly immersed in the sample chamber.

FIG. 10. Signal quality metrics to quantify imaging depth of Bone CLARITY. (FIG. 10A) MIP of a cleared mouse femur with estimates of imaging depth limit at different anatomical regions. The arrows indicate the direction of analysis and the calculated imaging depth. (FIG. 10B) Examples of isolated Sox9+ cells at different imaging depths and in different bone regions. $Sox9^+$ cells remain distinguishable at the deepest parts of the metaphysis and diaphysis, but signal loss is evident in the deeper parts of the epiphysis. The same analysis was repeated for a cleared mouse tibia (FIG. 10C) and vertebra (FIG. 10D). (FIG. 10E) The peak signal-to-noise ratio (PSNR) of isolated $Sox9^+$ cells. The dashed lines represent a qualitative estimate of where cells are no longer distinguishable from background noise, at a PSNR of around 24.

(FIG. 13A) No fluorescence signal is present in the emission spectrum of tdTomato (556 nm laser excitation) in the vertebral column of a wild-type mouse. (FIG. 13B) Using the same imaging settings as in panel (FIG. 13A), $Sox9^+$ mouse shows tdTomato expression even without tamoxifen induction. The fluorescence signal is primarily located at the endplates and attributed to leakage. (FIG. 13C) Using the same imaging settings as panel (FIG. 13A), $Sox9^+$ mouse shows high levels of tdTomato expression after tamoxifen induction.

DETAILED DESCRIPTION

Figure 1:
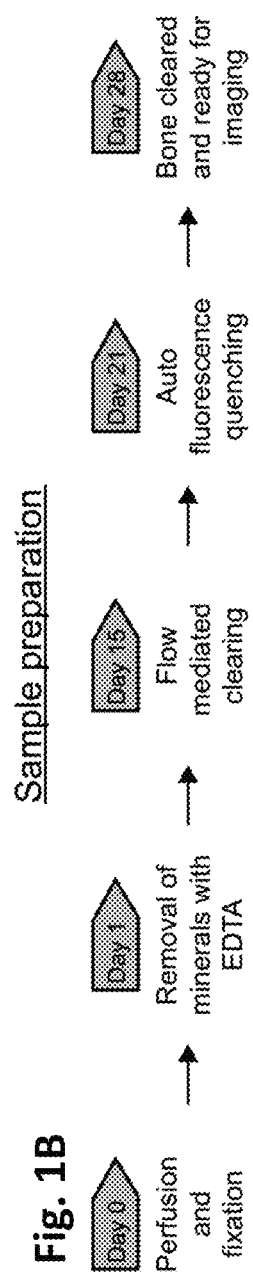
FIG. 1. Bone CLARITY renders intact bones transparent while preserving endogenous fluorescence.
Figure 1:
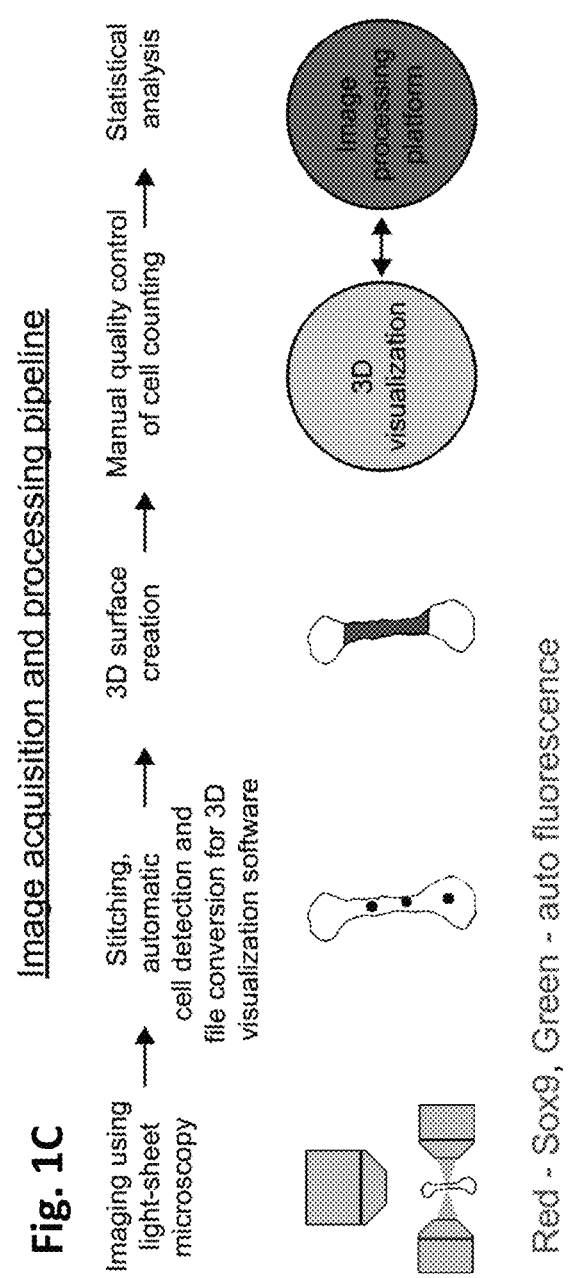
Figure 1:
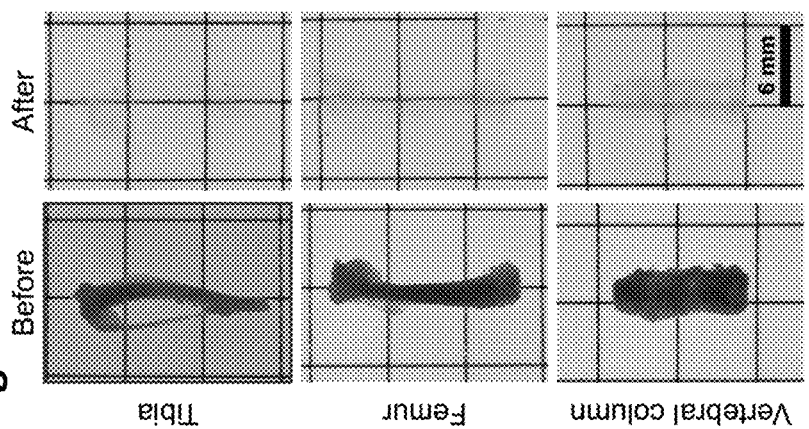
Figures 1, 1D, 1E:
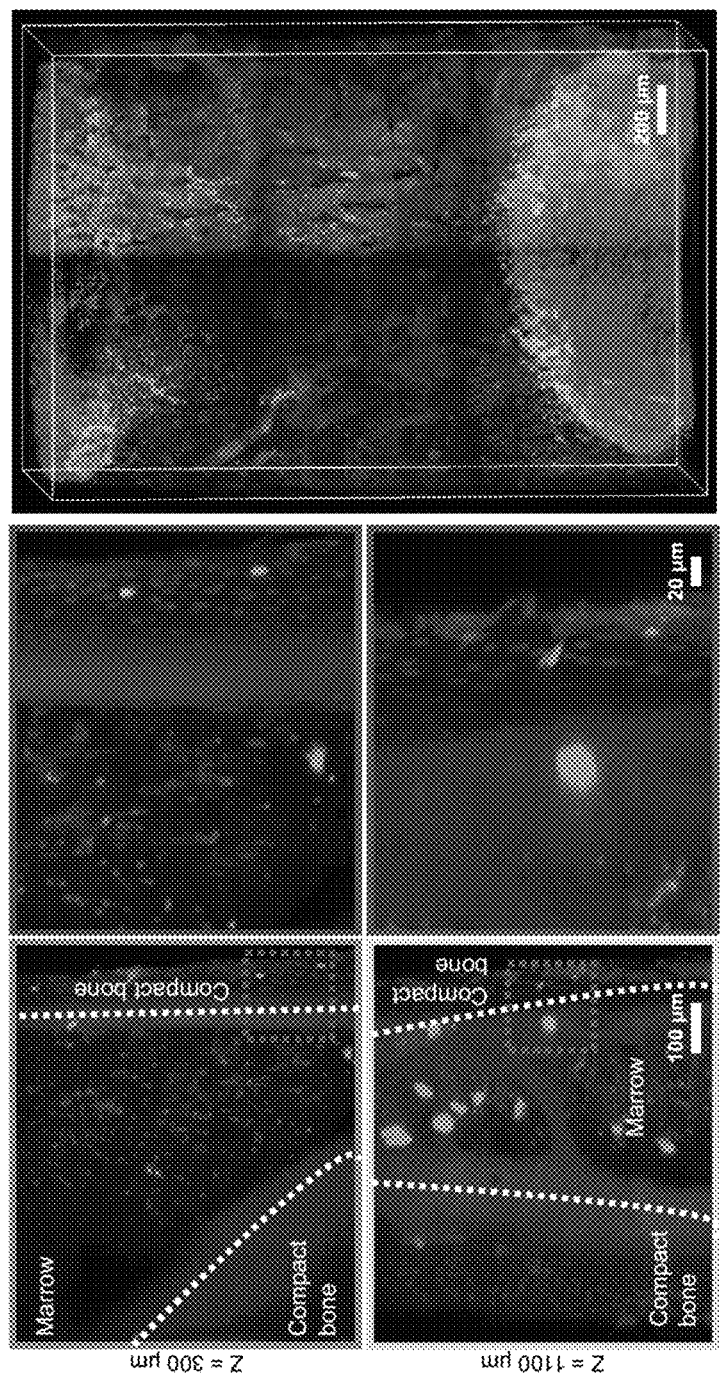
(FIG. 1D) Maximum intensity projection (MIP) fluorescence image of the tibia and zoomed-in digital slices (red, Sox9; and green, autofluorescence). Using Bone CLARITY, bones were imaged from one end to the other in the diaphysis (magnified images) and about 1.5 mm deep into the epiphysis. Dotted yellow and blue boxed regions in the MIP represent the area of zoom in the digital slices (30 mm thick). The purple and red dotted boxed regions in the digital sections represent the area that is shown with further higher magnification. The white dotted lines represent the boundaries of the compact bone.
(FIG. 1E) MIP fluorescence image of the vertebral body.

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* 22$^{nd}$ ed, Pharmaceutical Press (Sep. 15, 2012); Hornyak et al., *Introduction to Nanoscience and Nanotechnology,* CRC Press (2008); Singleton and Sainsbury, *Dictionary of Microbiology and Molecular Biology* 3$^{rd}$ ed., revised ed., J. Wiley & Sons (New York, N.Y. 2006); Smith, *March's Advanced Organic Chemistry Reactions. Mechanisms and Structure* 7$^{th}$ ed., J. Wiley & Sons (New York, N.Y. 2013); Singleton, *Dictionary of DNA and Genome Technology* 3$^{rd}$ ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, *Antibodies A Laboratory Manual* 2$^{nd}$ ed., Cold Spring Harbor Press (Cold Spring Harbor N.Y., 2013); Köhler and Milstein, *Derivation of specific antibody-producing tissue culture and tumor lines by cell fusion*, Eur. J. Immunol. 1976 July, 6(7):511-9; Queen and Selick, Humanized immunoglobulins, U.S. Pat. No. 5,585,089 (1996 December); and Riechmann et al., *Reshaping human antibodies for therapy*, Nature 1988 Mar. 24, 332(6162):323-7.

One skilled in the art will recognize many methods and materials similar or equivalent to those described herein, which could be used in the practice of the present invention. Indeed, the present invention is in no way limited to the methods and materials described. For purposes of the present invention, certain terms are defined below.

As used herein, PACT is an acronym for PAssive CLARITY Technique.

As used herein, PARS is an acronym for Perfusion-assisted Agent Release in Situ.

As used herein, RIMS is an acronym for Refractive Index Matching Solution.

As used herein, ePACT is an acronym for expansion-enhanced PACT.

As used herein, PACT deCAL is an abbreviation of the term PACT delipidation and decalcification of bone.

Several methodologies for tissue clearing have been proposed for large-scale 3D mapping of tissue macromolecular content. Each of these protocols offers distinct advantages, such as: preserving tissue architecture, accommodating standard histological techniques or creating a computational workflow for acquiring and/or reconstructing thick-tissue image stacks. Building on the prior CLARITY (Clear Lipid-exchanged Acrylamide-hybridized Rigid Imaging/Immunostaining/In situ hybridization-compatible Tissue hYdrogel) technique and concepts for generating extractable tissue-hydrogel hybrids (as referenced and described in U.S. patent application Ser. No. 14/447,607, filed Jul. 30, 2014, which is hereby incorporated by reference herein in its entirety as though fully set forth), the trio of PACT (PAssive CLARITY Technique), PARS (Perfusion-assisted Agent Release in Situ), and RIMS (Refractive Index Matching Solution) were developed to offer a user-friendly, rapid approach to rendering whole organs and whole organisms transparent. See U.S. Pat. Nos. 9,778,154, 9,778,155, U.S. patent application Ser. No. 14/935,279, U.S. patent application Ser. No. 15/239,724, PCT App. No. PCT/US2016/047430, each of which are fully incorporated by reference here. These methods preserve the macromolecular content of samples, enabling immunohistochemical, single-molecule RNA fluorescence in situ hybridization (smFISH), and small-molecule staining throughout thick tissues, stabilize tissue architecture, complement fluorescent labeling and imaging, and enable long-term storage.

A key challenge in developing high resolution optical access to bone is that the mammalian skeletal system consists of numerous bones of varying shapes and sizes that provide support to the body and protect internal organs from external physical stress. Different bone types harbor specialized physiological processes that are key for proper development and survival of the organism, such as replenishment of he-matopoietic cells, growth, and remodeling of the bone during healthy and diseased states. Traditionally, these processes have been investigated through methods that provide zero-dimensional (0D) or 2D information, such as fluorescence-activated cell sorting or analysis of histological sections. Quantitative 3D data of geometric features, such as volume and number of cells, can be obtained from histological sections with unbiased stereological methods. Although statistically robust, these methods are labor-intensive and provide no visualization of the 3D structures. The need for methods that provide 3D information to study the bone has long been recognized. Although methods, such as serial sectioning and milling, are valuable tools for understanding the structure of bone at the tissue level, these are destructive techniques that do not provide information at the cellular level and cannot be easily combined with other methods, such as im-munohistochemistry, to characterize cellular processes.

CLARITY was originally developed for soft tissues, such as the brain; recently, there has been a surge in optical clearing methods for a variety of applications (for example, profiling of tumor biopsies and brain tissue). Bone is a more complex histological sample, owing to its hard (mineral) and soft (bone marrow) tissue, and accordingly, osseous tissue has remained a challenge, despite some promising developments.

One method for investigating intact bones and their 3D microenvironments at sub-micrometer resolution is to render the tissue optically transparent. Bone transparency can be accomplished by coupling refractive index (RI) matching reagents with removal of minerals and lipids that scatter light. Most bone clearing literature is based on solvent clearing methods. These methods focus on RI matching and solvation of some lipids but do not remove minerals. In general, these solvent-based clearing methods have achieved an imaging depth of about 200 mm using two-photon microscopy. Murray's clearing method was recently modified to clear bisected long bones and achieved an imaging depth of about 600 mm with confocal microscopy. Despite these advances, manipulation and subsampling of the bone is required for deep imaging, thus disrupting the intact bone architecture. A key limitation of Murray's clearing method and its variants is that they quench endogenous fluorescence, minimizing their application with transgenic fluorescent reporter lines, which are used to highlight key cell populations within the bone and marrow. Moreover, bone is robust, marrow is fragile as overclearing would cause loss of fluorescence. Consequently, there is a need for a clearing method that maintains the intact bone structure, preserves endogenous fluorescence, and allows deeper imaging within intact bone.

The Inventors noticed that decalcification of bones by EDTA could, in principle, expand CLARITY applications to osseous tissues, but the Inventors only achieved modest optical access (200 to 300 mm). Here, the Inventors introduce Bone CLARITY, a specialized protocol that incorporates continuous convective flow during the clearing process, amino alcohol to minimize tissue autofluorescence, and an imaging procedure that minimizes RI variations in light-sheet microscopy. These improvements allowed achievement of whole-bone clearing with an imaging depth of up to about 1.5 mm while maintaining native tdTomato fluorescence and a signal-to-noise ratio (SNR) that permitted detection and 3D placement of single cells. The Inventors present a comprehensive platform based on whole-bone clearing, light-sheet imaging with a custom-built microscope, and dedicated computational methods for counting fluorescently labeled cells. The Inventors use this trio of methods to visualize and quantify the total number of osteoprogenitors contained within a volume of mouse bone and map their 3D spatial distribution in response to a sclerostin antibody (Scl-Ab), a bone-forming agent.

More specifically, using Bone CLARITY and a custom-built light-sheet fluorescence microscope to detect the endogenous fluorescence of Sox9-tdTomato$^+$ osteoprogenitor cells in the tibia, femur, and vertebral column of adult transgenic mice. To obtain a complete distribution map of these osteopro-genitor cells, the Inventors developed a computational pipeline that semiautomatically detects individual Sox9-tdTomato$^+$ cells in their native three-dimensional environment. The Inventors' computational method counted all labeled osteoprogenitor cells without relying on sampling techniques and displayed increased precision when compared with traditional stereology techniques for estimating the total number of these rare cells. The Inventors demonstrate the value of the clearing-imaging pipeline by quantifying changes in the population of Sox9-tdTomato-labeled osteoprogenitor cells after sclerostin antibody treatment. Bone tissue clearing is able to provide fast and comprehensive visualization of biological processes in intact bone tissue.

Tissue Preparation

With regard to tissue preparation, in various embodiments, an anesthetized (e.g. with Euthasol) subject is transcardially perfused with a perfusion solution that includes PBS (or an equivalently functioning alternative) at a concentration of 1× (1×PBS contains 10 mM $PO_4^{3-}$), or with a solution that includes 0.01-1.0 M PBS or phosphate buffer (PB), including 0.01 M PBS. In some embodiments, the solution including PBS or PB further includes heparin at a concentration of 1-20 U/ml, or 2-18 U/ml, or 4-16 U/ml, or 6-14 U/ml, or 8-12 U/ml, or 10 U/ml. In some embodiments, the hPBS or hPB further includes 0.1-1.0%, or 0.2-0.80%, or 0.3-0.6%, or 0.4-0.5% $NaNO_2$. In some embodiments, the hPBS solution includes 1×PBS, 0.5% $NaNO_2$ and 10 U/ml heparin ("hPBS"). In some embodiments, the heparinized phosphate-buffered solution includes 0.1 M PB, 0.5% $NaNO_2$ and 10 U/ml heparin ("hPB"). In certain embodiments, the solution used at this stage is from 0-25° C., or 4-23° C., or 6-21° C., or 8-19° C., or 10-17° C., or 12-15° C., or 13-14° C. In some embodiments, the solution is ice cold. In some embodiments, the pH range of the perfusion solution at this stage is 6-10, or 7-9, or 9, including pH 7.4. In some embodiments, the subject is transcardially perfused with hPBS or hPB until the perfusate drains clear from the right atrium. In some embodiments, the perfusion pressure (flow rate) during transcardial perfusion should approximate the physiological pressure of the subject's circulatory system, and thus could vary greatly from one animal subject to the next.

In some embodiments, the next step is to transcardially perfuse the subject with a fixative solution. In some embodiments, the fixative solution includes paraformaldehyde (PFA). Importantly, although PFA is specifically mentioned as a fixative that can be used throughout the present application, it is to be understood that in each instance in which PFA is mentioned, any comparable fixative to PFA could be used, including but in no way limited to Zinc formalin mixtures, Bouin and PFA supplemented with 0-2% glutaraldehyde. In some embodiments, the PFA solution includes 0.5-10%, or 1-9%, or 2-8%, or 3-7%, or 4-6%, or 5% PFA. In some embodiments, the PFA solution further includes 1×PBS or 0.1 M PB (or an equivalently functioning alternative). In some embodiments, the PFA solution includes 4% PFA in 1×PBS. In some embodiments, the PFA solution includes 4% PFA in 0.1 M PBS. In some embodiments, 10-500 ml or more, or 20-400 ml, or 40-300 ml, or 60-200 ml, or 80-100 ml is transcardially perfused at a rate of 1-100 ml/min, or 10-90 ml/min., or 20-80 ml/min. or 30-70 ml/min., or 40-60 ml/min, or 50 ml/min, depending upon the size and condition of the subject, and the physiological pressure of the subject's circulatory system. In some embodiments, the solution including PFA is introduced transcardially at a temperature of 0-25° C., or 4-23° C., or 6-21° C., or 8-19° C., or 10-17° C., or 12-15° C., or 13-14° C. In some embodiments, ice cold PFA solution is introduced. In some embodiments, the pH range of the fixative solution at this stage is 6-10, or 7-9, or 9, including pH 7.4. In certain embodiments, for initial perfusion-fixation, gravity alone may be used to draw hPBS (or hPB) and PFA through rodent vasculature.

In certain embodiments, the aforementioned solutions are used to incubate a bone-containing tissue of interest that has been excised from a subject, rather than introducing the solutions through the subject's vascular system as described above.

In certain embodiments, after the aforementioned treatments have been performed, a tissue sample containing bone ("bone sample") is excised from a subject (assuming it has not already been excised, as indicated above). In certain embodiments, the bone sample is rid of connective tissue using surgical instruments or gauze. In some embodiments the bone sample once removed or removed and rid of connective tissue is incubated in a solution that includes PFA. In some embodiments, the PFA solution is 1-8%, 2-6%, or 3-4% PFA. In some embodiments, the PFA solution is 4% PFA. In certain embodiments, the bone sample is incubated in PFA at this stage for 1-24 hours, 4-18 hours, 6-16 hours, 8-14 hours, or 10-12 hours. In some embodiments, the bone sample is incubated in PFA at a temperature of 1-35° C. or 2-28° C., or 4-20° C. In certain embodiments, the bone sample is incubated in PFA for 1-2 hours at room temperature. In certain embodiments, the bone sample is then incubated in PFA for 12-36 hours at 4° C. In some embodiments, the bone sample is incubated in PFA for 10-12 hours at 4° C. After the bone sample has been incubated in PFA, a PFA-fixed bone sample is formed.

Decalcification

In some embodiments, the bone sample is decalcified by transfer to a decalcifying solution including a calcium chelating agent. In some embodiments, the calcium chelating solution includes EDTA or EGTA, but other calcium chelating solutions could also be used without departing from the spirit of the invention. In some embodiments, bone samples are incubated in a calcium chelating solution (e.g. EDTA solution or EGTA solution) before any clearing solution. In some embodiments, the EDTA solution includes 0.025 M-1 M, or 0.05 M-0.75 M, or 0.075 M-0.5 M EDTA. In some embodiments, the EGTA solution includes 0.025 M-1 M, or 0.05 M-0.75 M, or 0.075 M-0.5 M EGTA. In some embodiments, the EDTA solution into which the bone sample is transferred includes 0.1 M, 0.2 M or 6, 7, 8, 9, 10, 11, 12, 13, or 140/o EDTA. In some embodiments, the EDTA solution includes 10% EDTA. In some embodiments, the EGTA solution into which the bone sample is transferred includes 0.1 M, 0.2 M 6, 7, 8, 9, 10, 11, 12, 13, or 14% EGTA. In some embodiments, the EGTA solution includes 10% EGTA. In certain embodiments, the EDTA or EGTA solution further includes PBS or PB (or a functional equivalent). In various embodiments, the PBS solution includes 0.005-0.015 M PBS, including 0.01 M PBS. In some embodiments, the EDTA solution into which the bone sample is transferred includes 0.1M EDTA or 10% EDTA in 1×PBS, and the solution is at pH 6.5-9.5, 7-9, or 8.0. In various embodiments, the bone sample is incubated in the EDTA or EGTA solution for a period of 0.1-21 days or more (depending upon the size and density of the bone) 0.2-18 days, or 0.3-16 days, or 0.4-10 days, or 0.5-6 days, or 0.4-5 days, or 0.5-4 days, or 0.6-3 days, or 0.7-2 days, or 0.8-1 day. In some embodiments, the bone sample is incubated in the EDTA or EGTA solution for a period of 5, 6, 7, 8, 9, 10, 11, 12, 13, 14, 15, 16, 17, 18, 19, or 20 days. In some embodiments, the bone sample is incubated in the EDTA or EGTA solution for a period of 14 days. In certain embodiments, the EDTA or EGTA solution is changed 0-24, 1-16, 2-12, 3-10, 4-8, or 5-7 times per day. In some embodiments, the EDTA or EGTA solution is changed, or exchanged, daily. In some embodiments, incubation in the chelating solution (e.g., EDTA, EGTA) includes continuous stirring or flow exchanges the EDTA volume daily. In some embodiments, the bone sample is incubated in the calcium chelating solution (e.g. EDTA or EGTA) until it becomes soft and flexible, indicating that the bone has become substantially decalcified, thereby forming a substantially decalcified bone sample.

Formation of a Bone-Hydrogel Matrix

In some embodiments, the next step in bone clearing is to applying a hydrogel monomer solution to form a bone tissue sample hydrogel matrix before decalcification. In some embodiments, a bone-hydrogel matrix is formed after the decalcification procedure described herein. In some embodiments, the PFA-fixed bone sample is transferred into a container containing a hydrogel solution. In some embodiments, the hydrogel solution is a hydrogel monomer solution that includes acrylamide at a concentration of from 1-20%, or 2-18% or 3-17%, or 4-16%, or 5-15%, or 6-14%, or 7-13%, or 8-12%, or 9-11%, or 10%. In some embodiments, the hydrogel solution includes PBS (or functional equivalent thereof). In certain embodiments, the hydrogel monomer solution includes A4P0. In certain embodiments, the hydrogel monomer solution further includes PFA at a concentration of 0.5-10%, or 1-9%, or 2-8%, or 3-7%, or 4-6%, or 5%. In certain embodiments, the hydrogel monomer solution does not include PFA. In some embodiments, the hydrogel monomer solution does not include bisacrylamide. In various embodiments, the hydrogel monomer solution includes an polymerization initiator, including thermoinitiators and photoinitiators. For example, thermoinitiators such as VA-044 (2,2'-Azobis[2-(2-imidazolin-2-yl)propane]dihydrochloride) can be used at concentrations of 0.05% to 1.0%, including 0.25%. In some embodiments, the bone-hydrogel sample incubating in the clearing solution is agitated during incubation by rocking, mixing, stirring, or continuous flow. For examples, an A4P0 hydrogel can include 4% acrylamide, 0% PFA, and 0.25% thermoinitiator VA-044.

In some embodiments, in order to increase the level of crosslinking without the addition of bisacrylamide or PFA to the hydrogel monomer solution, the hydrogel-infused bone sample is significantly degassed by removing residual oxygen from the bone sample and any container in which it has been placed. In some embodiments, degassing is accomplished by replacing oxygen in the solution and environment surrounding the bone sample with nitrogen. In some embodiments, the bone sample is incubated in a hydrogel monomer solution for 1 hour-5 days or more, 6 hours-3 days, or 12 hours-2 days. For large bones (e.g. a human femur or larger), incubation of one week to more than one month may be required, depending upon the size and density of the particular sample. For example, samples can be degassed through nitrogen gas exchange for 5 minutes and initiating polymerization by incubation for 3 hours at 37° C.

In some embodiments, the bone sample is incubated in hydrogel monomer solution at a temperature of 0-10° C., 2-8° C., or 4-6° C. In some embodiment, the bone sample is incubated at a temperature of 4° C. for 12 hours. The above-described hydrogel embedding results in a bone-hydrogel sample. In some embodiments, the bone-hydrogel sample can be used for subsequent analysis, without executing further steps described herein. In other embodiments, the ensuing steps can be implemented.

Tissue Delipidation

In certain embodiments, after the previously described hydrogel embedding, or after arriving at a bone tissue sample hydrogel matrix by any other method known in the art (including by PARS or any other protocols discussed or referenced herein), the resulting bone-hydrogel sample is incubated in a clearing solution that includes a detergent. In some embodiments, the detergent may include SDS. In some embodiments, saponin, Triton X-100, Tween-20 and the like may be used as an alternative or in addition to SDS. In some embodiments, the clearing solution includes 1-20% SDS, or 2-18% SDS, or 3-17% SDS, or 4-16% SDS, or 5-15% SDS, or 6-14% SDS, or 7-13% SDS, or 8-12% SDS, or 9-11% SDS, or 8% SDS. In some embodiments, the clearing solution that includes SDS further includes 0.005-0.015 M PBS or PB, including 0.01 M PBS or PB (or a functional equivalent). In some embodiments, clearing may be performed in any convenient buffer that is compatible with the selected clearance method, e.g., saline, phosphate buffer, phosphate buffered saline (PBS), sodium borate buffer, boric acid buffer, citric acid buffer and the like. In some embodiments, the clearing solution that includes SDS includes 1×PBS (or a functional equivalent). In an embodiment, the clearing solution that includes SDS includes 6, 7, 8, 9, 10, 11, or 12% SDS in 1×PBS, including 8% SDS. In some embodiments, the clearing solution that includes SDS has a pH of 6.5-9.5, or 7.0-9.0, or 8.0. In some embodiments, the clearing solution includes 8% SDS in 1×PBS and it has a pH of 7.4. In some embodiments, the bone-hydrogel sample incubating in the clearing solution is agitated during incubation by rocking, mixing, stirring, or continuous flow. In certain embodiments, this stage of incubation is carried out at a temperature of 25-42° C. In some embodiments, the temperature at which the bone-hydrogel sample is incubated in the clearing solution is 37° C. In certain embodiments, the incubation temperature is maintained by placing a container containing the bone-hydrogel sample and clearing solution in a heated water bath. In some embodiments, the sample is incubated in the clearing solution for 1 hour-21 days, 2 hours-15 days, 3 hours-12 days, 6 hours-4 days, 12 hours-3 days, 3-7 days, or 3-5 days. Importantly, the rate of tissue clearing depends on several parameters, including the inherent structural and biochemical properties of the tissue sample, the volume of the tissue sample, the hydrogel pore size and density of tissue-hydrogel crosslinking, and the clearing set-up (e.g. SDS concentration, incubation temperature, and pH of clearing buffer). For example, a vertebral body bone can be delipidated in 4 days, and a long bone can be delipidated in 5 days.

In various embodiments, the substantially cleared decalcified, delipidated bone is incubated in a washing solution for a period of 1-72 hours, or 6-48 hours, or 8-24, or 24-72 hours, or 48 hours. In some embodiments, incubation at this stage is for a period of 24 hours. In some embodiments the washing solution includes PBS (or a functional equivalent). In some embodiments, 0.005-0.015 M PBS or PB, including 0.01 M PBS or PB (or a functional equivalent) is used. In some embodiments, 1×PBS is used at this stage. In some embodiments, the pH range of the solution in which the tissue sample is incubating at this stage is 6-10, or 7-9, or 9. In certain embodiments, the pH of the solution in which the tissue sample is incubating at this stage is 9. In some embodiments, the PBS (or alternative buffer) is exchanged 1-10 times or more per day, 2-8 times per day, 3-6 times per day, or 4-5 times per day. In some embodiments, the substantially decalcified bone is agitated during incubation by rocking, mixing, stirring, or continuous flow. For example, 3 exchanges can be performed over a 2 day (i.e., 48-hour) incubation period.

After this stage of treatment, the washed substantially cleared decalcified, delipidated bone sample is subject to heme removal. In various embodiment, the washed substantially declassified bone sample is subject to heme removal by incubation in a heme removal solution that includes includes an amino alcohol. In some embodiments, the amino alcohol is N,N,N',N'-Tetrakis(2-Hydroxypropyl)ethylenediamine. In some embodiments, the solution includes N,N,N',N'-Tetrakis(2-Hydroxypropyl)ethylenediamine in an amount ranging from 1-50%, 5-25%, 10-20%, or 20-30% w/v, including 25% w/v. In some embodiments the solution includes 25% w/v of N,N,N',N'-Tetrakis(2-Hydroxypropyl)ethylenediamine. In some embodiments, the solution further includes a buffer described herein (e.g. PBS or PB). In some embodiments, the pH range of the solution containing the amino alcohol is 6-10, including 9. For example, the solution containing the amino alcohol includes 25% w/v of N,N,N',N'-Tetrakis(2-Hydroxypropyl)ethylenediamine in 0.01M PBS at pH 8. In some embodiments, the washed substantially decalcified bone is agitated during incubation by rocking, mixing, stirring, or continuous flow. In certain embodiments, the solution is useful for optical clearing of lipids and blood cells in the bone-containing tissue sample. In some embodiments, the solution including the amino alcohol can be applied to the bone-containing tissue before and/or after treating the bone-containing sample with a calcium chelating agent as described above.

After heme removal, the heme removed cleared bone sample, washed again in a second wash step, according to the passage describing wash step.

Considering that bone consists of approximately 16% collagen, in certain embodiments, bone is incubated in collagenase before or after any of the preceding clearing steps, in order to disrupt the collagen matrix.

In various embodiments, the decalcification step of incubating in a calcium chelating agent (e.g. EGTA and/or EDTA) may occur before or after delipidation. Further, decalcification and/or delipidation may be repeated, as necessary. Thus, in some embodiments, bone clearing may be achieved by decalcification followed by delipidation. In other embodiments, bone clearing may be achieved by delipidation followed by decalcification and optionally one or more additional iterations of delipidation with or without additional decalcification.

Single-Cell Phenotyping of Cleared Tissues

The compositions and methods described above are amenable to most standard immunohistochemical protocols, including those involving one or more of a wide range of small-molecule dyes, primary antibodies, secondary antibodies, fluorescent labels, and other markers. Examples of nucleic acid stains that may be useful include, but are in no way limited to, dapi, Draq5, To-Pro and the like. Examples of antibodies that may be useful include, but are in no way limited to, those specific for osterix, collagen type I and IV, NG2 chondroitin sulfate proteoglycan, osteopontin, CD45, endomucin and the like. Examples of collagen stains that may be useful include, but are in no way limited to, picrosirius, trichrome, H&E, reticulin silver stain, tartrate resistant acid phosphatase for osteoclasts and alkaline phosphatase for osteoblasts In certain embodiments, the bone-containing tissue can be incubated with a primary antibody cocktail in an IHC buffer. In some embodiments, a primary antibody dilution of 1:10-1000 or more, 1:20-500, 1:100-400, or 1:200-300 is used. In some embodiments, the bone-containing tissue can be incubated in a primary antibody cocktail in an IHC buffer for 0.01-15 days, 0.5-10 days, 1-5 days, or 2-4 days. In some embodiments, this incubation is performed at 4-42° C., 6-40° C., 8-38° C., 10-36° C., 12-34° C., 14-32° C., 16-30° C., 18-28° C., 20-26° C., or 22-24° C. In some embodiments, the bone containing tissue is shaken or otherwise agitated during incubation.

In certain embodiments, after the bone containing tissue has been incubated in a primary antibody and/or stain (depending upon the protocol), unbound antibody and/or stain is removed by washing the bone containing tissue in an excess volume of washing buffer. In some embodiments, the washing buffer includes PBS (or a functional alternative). In some embodiments, the washing buffer includes 1×PBS. In some embodiments, the washing buffer is exchanged 0-20 or more, 2-18, 4-16, 6-14, or 8-10 times per day for a period of 0.1-10, 0.5-8, 1-6, 2-4, or 3 days. In some embodiments, sodium azide and/or alternative antimicrobial agents are included in the washing buffer.

In certain embodiments in which a secondary antibody is required, the primary antibody labeled (and optionally stained) bone-containing tissue can be incubated in a solution that includes a secondary antibody. In some embodiments, a secondary antibody dilution of 1:10-1000 or more, 1:20-500, 1:100-400, or 1:200-300 is used. In some embodiments, incubation in the solution containing the secondary antibody cocktail in an IHC buffer is performed for 0.01-15 days, 0.5-10 days, 1-5 days, or 2-4 days. In some embodiments, this incubation is performed at 4-42° C., 6-40° C., 8-38° C., 10-36° C., 12-34° C., 14-32° C., 16-30° C., 18-28° C., 20-26° C., or 22-24° C. In certain embodiments, Fab fragment secondary antibodies are used. In some embodiments, the PACT-deCAL cleared bone is shaken or otherwise agitated during incubation.

In certain embodiments, after the bone-containing tissue has been incubated in the secondary antibody, unbound secondary antibody is removed by washing the bone-containing tissue in an excess volume of washing buffer. In some embodiments, the washing buffer includes PBS (or a functional alternative). In some embodiments, the washing buffer is 1×PBS. In some embodiments, the washing buffer is exchanged 0-20 or more, 2-18, 4-16, 6-14, or 8-10 times per day for a period of 0.1-10, 0.5-8, 1-6, 2-4, or 3 days. In some embodiments, sodium azide and/or alternative antimicrobial agents are included in the washing buffer at this stage.

In some embodiments, one or more of the foregoing passive histology steps are performed prior to clearing the bone-containing tissue. In some embodiments, or more of the foregoing passive histology steps are performed after clearing the bone containing tissue.

RIMS (Refractive Index Matching Solution) for Cleared Bone

Whether or not the preceding immunohistochemical labeling steps are performed, one or more RIMS, described in detail below, can be used in conjunction with cleared bone.

In some embodiments, the refractive index (RI) of the cleared bone is calculated by using a refractometer according to manufacturer instructions. A sample-optimized RIMS formulation can be prepared by adjusting the amount of Histodenz™ (or comparable alternative solution) dissolved in an appropriate buffer, which may include, but is in no way limited to PB or PBS (or functional equivalent). In some embodiments, the buffer includes 0.005-0.1 M, 0.01-0.04 M, or 0.02 M PBS. In some embodiments, the buffer includes 0.002-0.2 M, 0.005-0.15 M, 0.01-0.1 PB. In some embodiments, the buffer includes 0.02 M PB. In some embodiments, the buffer includes 0.01-0.05% sodium azide. In some embodiments, a RIMS formulation with an RI of 1.38-1.5, 1.4-1.48, or 1.48-1.49 may be used, such as 1.38, 1.43, and 1.47. In some embodiments a graded series of RIMS formulations is sequentially introduced with daily stepwise RIMS exchanges, including formulations of RIMS with RI of approximately 1.38, approximately 1.43, and approximately 1.47. Approximations for these embodiments may be within ±0.01.

In some embodiments, the cleared bone is processed through a graded series of RIMS incubations, with approximately 2-48 hours, 4-36 hours, 6-24 hours, 8-18 hours, or 10-15 hours at each stage. In some embodiments, cleared bone is incubated at each stage for 24 hours. In some embodiments, the first stage is incubation in RIMS with an RI of approximately 1.38. In some embodiments, the next stage is incubation in RIMS with an RI of approximately 1.43. In certain embodiments, the final stage is incubation in RIMS with an RI of approximately 1.47. One of skill in the art would appreciate that less than three or more than three RIMS with progressively increasing RIs could be used to achieve the final appropriate RI for the bone tissue. In some embodiments, the sample is submerged in excess RIMS and incubated at RT until it reaches the desired transparency. The time for incubation will vary depending upon the specific characteristics of the bone sample. In some embodiments, the cleared bone sample is agitated during incubation by rocking, mixing, stirring, or continuous flow. In some embodiments, incubation times may be shortened significantly by placing samples on a nutating mixer (or other means of agitation).

In some embodiments, the cleared bone is incubated in excess RIMS at each stage at a temperature of 4-42° C., 6-40° C., 8-38° C., 10-36° C., 12-34° C., 14-32° C., 16-30° C., 18-28° C., 20-26° C., 21-23° C., or 22-24° C. until it reaches the desired transparency. In some embodiments incubation for one or more of the aforementioned stages occurs at a temperature of 20-22° C. In some embodiments, incubation may be significantly shortened by incubating on a nutating mixer or the like. In some embodiments, alternative mounting solutions can be substituted for RIMS to effectively image cleared bone, as described in the examples set forth herein. In some embodiments, RIMS treated cleared bone may be stored for three months or longer in RIMS. In some embodiments, RIMS treated samples are kept in an airtight container at 20-22° C. and protected from the light. Alternatively, when short-term storage at 4° C. is required, samples may be mounted in cRIMS (as described in the examples set forth herein) and stored in a preferably dry and preferably airtight container. In some embodiments, the RIMS treated cleared bone is allowed to equilibrate in RIMS prior to imaging when sub cellular or cellular level imaging is to be performed. In some embodiments, if coarse cellular phenotyping and/or rapid visualization is desired, then a shorter incubation may be performed. In some embodiments, sRIMS (as described in the examples set forth herein) is used instead of RIMS.

In some embodiments, the refractive-index homogenized RIMS treated cleared bone is transferred to an airtight container filled with fresh RIMS (or an alternative mounting media such as sRIMS or 87% (vol/vol) glycerol). In some embodiments, the bone sample is then degassed, by using a needle connected to a vacuum line or by another method. In some embodiments, sodium azide and/or an alternative antimicrobial substance is added to the RIMS (or alternative substance described herein)-treated cleared bone.

In some embodiments, after the RIMS treatment described above (or a comparable treatment) is performed, the cleared bone is mounted and imaged with a confocal microscope, a light sheet fluorescent microscope, a single-photon microscope, an epi-fluorescent microscope, a dissecting microscope, a wide-field fluorescence microscope with ApoTome, or another type of microscope useful for a particular desired application. In various embodiments, the aforementioned mentioned methods allow for optical access, imaging depth of below 5, 10, 50, 100, 200 and 300 mm.

In some embodiments, to image cleared bone-containing samples with a standard microscopy set-up (e.g. a single photon confocal microscope), a multi-immersion objective is used with a refractive index correction collar to match the RI of the mounted bone-containing sample ~1.47. In some embodiments, for immersion media, glycerol with the same RI as the mounting RIMS is used. Optimum acquisition parameters are determined and applied. Acquisition parameters (e.g. PMT gain, laser power and scanning speed) are optimized for each sample based on the desired final image quality.

Further described herein a microscopy platform for visualization and imaging processing for visualization. In various embodiments, the microscopy platform includes two light sheets that illuminate the sample from opposite directions, optionally include one or more confocal slits. In various embodiments, one selects the preferable illumination direction for markedly reduced scattering. In various embodiments, one minimizes acquired images in a Z-stack. In various embodiment, imaging processing includes an algorithm to divide 2D images that make up the Z-stack (or depth scan) into n small overlapping regions, and then adaptively thresholds the 2D images into binary images on the basis of the local mean and SD of fluorescence. In various embodiments, the resulting binary 2D images are further subjected to morphological operations to eliminate noise and discontinuity within a cell and all of the 2D binary images are then combined into a 3D matrix. In various embodiments, image processing includes quantifying imaging depth at different anatomical regions of the bone, including assessed cell detection in several anatomically distinct regions using a Peak SNR (PSNR) metric (equation 1). For example in an individual anatomical region, the starting point (0 μm) of the sample can be defined as the first depth that bone tissue filled at least 50% of the field-of-view. Selection of at least 10 isolated Sox9$^+$ cells along the image stack and calculation of PSNR indicates an area of 0.123 mm$^2$ and 0.086 mm$^2$ (for long bones and vertebrae, respectively) was used for the region around the cell. Under such circumstances, the minimum PSNR for cell detection was 24, allowing for image bone tissue to a depth of approximately 1.5 mm.

EXAMPLES

Example 1

Study Design

The objective of this study was to enable the visualization and quantification of cell population in an intact bone tissue by developing and integrating tissue clearing, fluorescence microscopy, and a computation pipeline. Experimental and control animal cohorts were chosen based on preliminary data that suggested a large effect size. All transgenic animals used in this study are as described in the Animals section. All wild-type animals used in this study were C57BL/6. To characterize the density of $Sox9^+$ cells and distribution within the femur, tibia, and vertebral column, male trans-genic animals of 6 to 7 weeks of age received a 2 mg of tamoxifen intraperitoneally on day 1 of the experiment to enable expression of a native fluorescent gene for 7 days before culling. For the study of the effects of Scl-Ab on total number of osteoprogenitor cells, a cohort of 7-week-old male trans-genic animals were treated with Scl-Ab at 100 mg/kg (subcutaneously) on day 1 and again at 100 mg/kg (subcutaneously) 4 days later with tamoxifen induction at 2 mg (intraperitoneally), before culling on day 9 of the study. The Scl-Ab was provided by Amgen. During cell counting, all manual quantification is performed in a blind manner to eliminate observer bias. Animals were randomly assigned to groups for experiments. Raw data values for cell counts are reported in the Supplementary Materials.

Example 2

Animals

A transgenic Sox9-CreERT2 mouse (RIKEN BioResource Center, #RBRC05522) was crossed to a Rosa26-loxP-stop-loxP-tdTomato (R26R-tomato, JAX7914) reporter mouse to generate Sox9-CreERT2-R26-tdt. Sox9-CreERT2-R26-tdt mice aged 6- to 7-week-old were used in the experiments involved in labeling Sox9 cells (n=18). The labeling was achieved by intraperitoneal injection of 2 mg of tamoxifen, which was dissolved first in 100% ethanol then in sunflower seed oil (Sigma-Aldrich, #S5007) overnight at 60° C. Mice were genotyped by polymerase chain reaction. All mice were analyzed in mixed backgrounds. Mice were group-housed in sterile, ventilated micro-isolator cages on corn cob bedding in a facility accredited by the Association for Assessment and Accreditation of Laboratory Animal Care. All procedures were conducted in compliance with the *Guide for the Care and Use of Laboratory Animals* approved by Massachusetts General Hospital's Institutional Animal Care and Use Committee. Animals were provided ad libitum access to pelleted feed (LabDiet 5010) and water (Standard drinking water of Boston, Mass.; pH 7.8) via Hydropac. Animals were maintained on a 12-hour light/12-hour dark cycle in rooms at 64° to 79° F. with 30 to 70% humidity under pathogen-free conditions.

Example 3

Bone deCAL CLARITY Protocol

Figure 5:
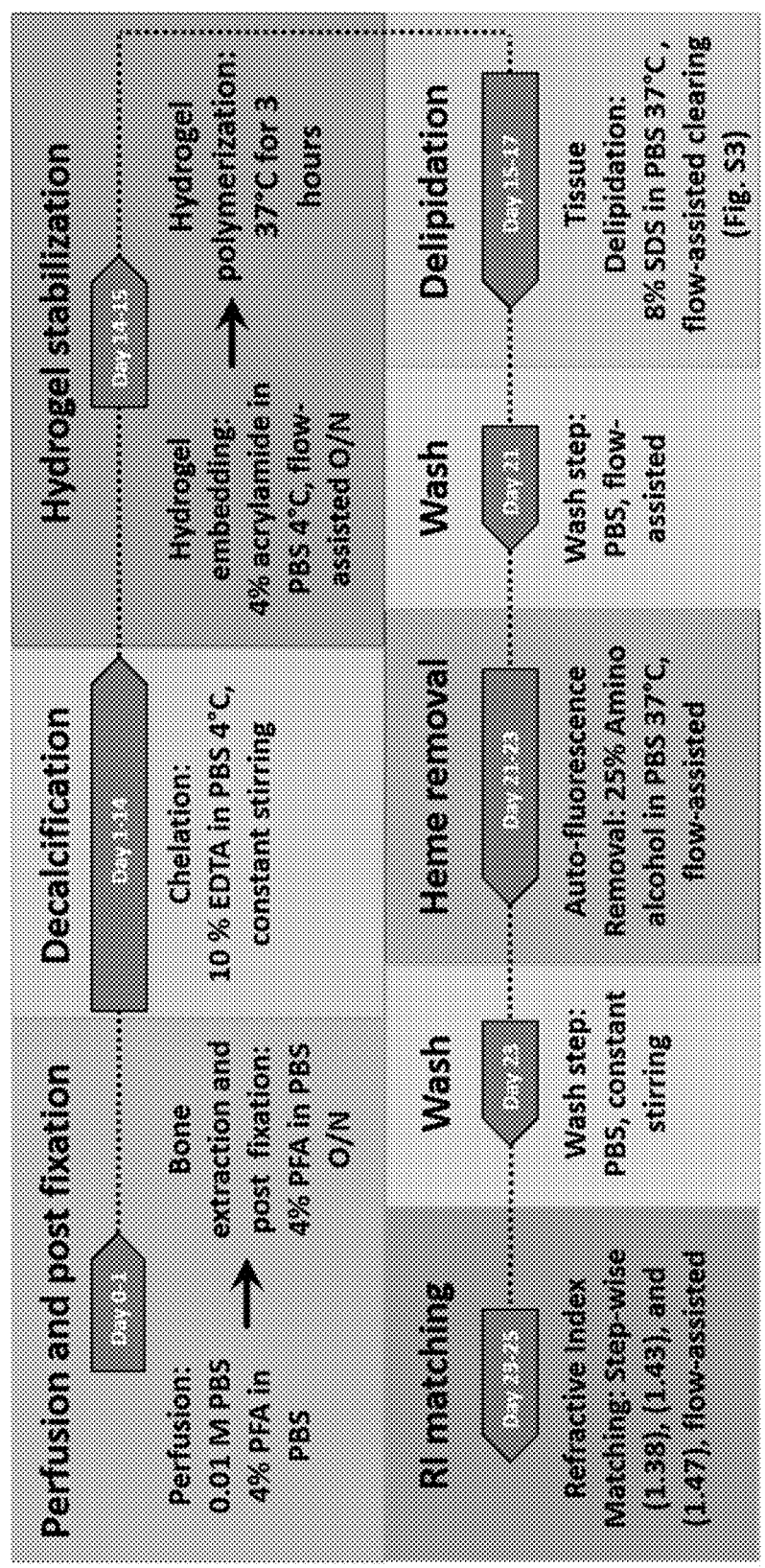
FIG. 5. Bone CLARITY clearing process. As a first step (blue) in Bone CLARITY method transcardial perfusion is performed with 0.01M PBS, pH 7.4, and 4% paraformaldehyde (PFA) in PBS, pH 7.4. Hard-tissue is then extracted and post-fixed with 4% PFA in PBS, pH 7.4, overnight at 4° C. Hard-tissue is then decalcified (orange). During this step, daily-exchange of 10% EDTA in PBS, pH 8, at 4° C. under constant stirring is performed Hydrogel stabilization to prevent protein loss is carried out (purple). The tissue is incubated in a hydrogel composed of 4% acrylamide with 0.25% VA044 in PBS at 4° C. under constant stirring overnight. Afterwards, the hydrogel is degassed with nitrogen gas and polymerized at 37° C. Delipidation is carried out with 8% SDS in PBS. pH 7.4 at 37° C. under constant stirring (green). A wash step with PBS is performed before heme removal from the tissue (first grey) Heme removal is performed with 25% amino alcohol in PBS, pH 9, at 37° C. under constant stirring (red stage). A second wash step is performed on the tissue (second grey). Finally, the tissue is refractive index matched to 1.47 through daily step-wise buffer exchange (blue stage).

The clearing process is summarized in FIG. 5. After euthanization, mice were perfused transcardially with 0.01 M phosphate-buffered saline (PBS) (Sigma-Aldrich, #P3813) followed by 4% paraformaldehyde (PFA) (VWR, #100496-496), and the femurs, tibias, and L3 to L5 vertebral columns were extracted. The bones were postfixed overnight in 4% PFA. To enhance clearing of hard-tissue, the Inventors extended the demineralization phase to 2 weeks with 10% EDTA (Lonza, #51234) in 0.01 M PBS (pH 8). During the demineralization phase, samples were kept under constant stirring in histology cassettes (Electron Microscopy Sciences, #70077-W) at 4° C. with fresh EDTA buffer exchanges daily. Next, the decalcified bones were embedded in a hydrogel matrix (A4P0), which consists of 4% acrylamide (Bio-Rad, #1610140), 0% PFA, and 0.25% thermoinitiator (Wako Chemicals, VA-044), in 0.01 M PBS overnight at 4° C. The samples were degassed through nitrogen gas exchange for 5 min and polymerized for 3 hours at 37° C. After structural reinforcement with the A4P0 hydrogel, deli-pidation was performed with 8% SDS in 0.01 M PBS (pH 7.4) for 4 or 5 days (vertebral body and long bones, respectively) at 37° C. under constant stirring (FIG. 7). The samples were then washed for 48 hours in 0.01 M PBS with three buffer replacements. The amino alcohol N,N,N', N'-tetrakis(2-hydroxypropyl)ethylenediamine (Sigma-Aldrich, #122262-1L) was added at 25% w/v in 0.01 M PBS (pH 9) for 2 days at 37° C. under constant stirring for the purpose of decolorization of the tissue through heme group removal. Last, the bones were washed with 0.01 M PBS for 24 hours and subsequently immersed in RI matching solution (RIMS). The bones were gradually immersed in RIMS with an RI of 1.47 through daily stepwise RIMS exchange with RIMS 1.38, 1.43, and finally, 1.47. The Inventors observed the exclusion of bis-acrylamide as important to have enough porosity for bone so hydrogel elements make it to the marrow and preserve it.

Example 4

Light-Sheet Microscopy Imaging

Before imaging, the sample was placed in the LSFM sealed immersion chamber for at least 3 hours, allowing the RIMS solution in the chamber to equilibrate with the residue RIMS in the bone sample. To minimize optical aberrations, the Inventors measured the RI of the RIMS solution, and the correction collar on the objective lens (10× CLARITY objective lens with numerical aperture of 0.6; Olympus XLPLN10XSVMP) was set accordingly. To image the entire bone, the Inventors acquired multiple tiles with 10% overlap. Typically, the femur, tibia, and vertebral body required 13×5, 11×5, and 3×2 tiles, respectively (vertical×horizontal). In a calibration stage that took place before the scan, the following parameters were defined for each tile: (i) light-sheet illumination direction; the LSFM has two light sheets that illuminate the sample from opposite directions. Selecting the preferable illumination direction markedly reduced scattering. (ii) The start and end point of the Z-stack: this step was carried out to minimize the number of acquired images in an already big data set (50 to 500 GB). (iii) The focus points of the detection objective along the scan were defined to mitigate RI variations along the scan that created out-of-focus aberrations. Once the calibration stage was completed, the bone was imaged with a frame rate of 22 frames per second and bit depth of 16 bits. The acquired data set size depends on the sampled voxel size. For a voxel size of 0.585×0.585×2 mm3, the tibia and femur produced ~250 GB of data per color channel, whereas the vertebral body produced ~30 GB of data per color. Generally, the data sets are down-sampled after acquisition for processing; the typical voxel sizes are 1.17×1.17×2 mm3 and 2.34×2.34×2 mm3 for the vertebral column and long bones, respectively.

All experimental and control groups were imaged with the same laser power. For Images that were acquired deep in the bone and when the SNR changed within the distance from the bone boundary, the contrast and gamma were adjusted in the displayed images. The gamma adjustment was performed to visualize cells that exhibit both low and high intensity within the same field of view. Images from the vertebra (Sox9+ and Tam+ group) are representative of 13 vertebrae from 13 mice. Images from the tibia and femur (Sox9+ and Tam+ group) are representative of five tibias and five femurs from five mice.

Example 5

Statistical Analysis

All statistical analyses were performed using GraphPad Prism version 7.01. For FIGS. 2C and 4 (E, I, and J), mean values for each group were compared using an unpaired t test. In all graphs, data points per individual animal trial with the mean value and SEM are shown.

Example 6

Supplementary Methods

Simulated Stereology:

To investigate the variability between 3D counting and 2D section counting, the Inventors performed a series of simulated stereology experiments using the Inventors' 3D datasets. To start, the coordinates of each cell center were imported to MATLAB as a list, and the VOI was imported to MATLAB as a binary mask. From the binary mask, the volume of each 2D section was calculated by accumulating the number of pixels in the 2D section and multiplying it by the voxel size. Then, a simple random sampling stereology experiment was simulated by stochastically selecting N digital sections (6 μm thick) from the entire VOI. Only cells whose centroids were within the volume of the selected digital sections were counted, this guarantees that each cell will be counted only once and cell will not be over represented. To calculate the cell density, the total number of counted cells in the selected digital sections were divided by their accumulated volume. From sampled cell density and the known volume of the entire bone, the total number of cells in the bone was estimated. In order to calculate the coefficient of variation, each experiment was repeated 5 times and the standard deviation of the experiments was divided by the total cell number of the volume. To reflect modern stereology sampling techniques, the Inventors also simulated systematic uniform random sampling (SURS) stereology experiments. As compared to simple random sampling, SURS has a stricter subset of possible samplings. Rather than looking at any random subset of slices, SURS requires sampling the tissue with a fixed interval, while the first starting slice is randomly selected (FIG. 3A). In order to compare SURS with simple random sampling, each SURS experiment consisted of a specific number of digital slices. Since a specific number of digital slices can be attained by a variety of sample intervals, the minimum interval that would yield the desired number of slices was selected. Once the digital sections were selected for SURS, the cell density was calculated in the same manner as simple random sampling. To calculate the coefficient of variation, each SURS experiment was repeated for 5 random starting positions. FIG. 3C shows only numbers of slices that yielded at least 5 possible starting positions.

Quantifying the effect of amino alcohol (related to FIG. 6): High levels of auto-fluorescence can overshadow elements of interest and lead to false inclusion of features. Intensity data from the mouse femur and tibia before and after treatment with amino alcohol (N,N,N',N'-tetrakis(2-hydroxypropyl) ethylenediamine) were analyzed. The starting depth (0 μm) was defined as the first section that contained both sufficient compact bone and marrow for analysis. Then, for 7-9 depths along the imaging dimension, two areas (~1000 μm2) were extracted. The first area exclusively contained compact bone, while the other exclusively contained marrow. The mean intensities of the two areas (marrow and compact bone) were then calculated. The mean intensity ratio (marrow versus compact bone) was used to quantify the amino alcohol effect on quenching auto-fluorescence in the marrow, since amino alcohol operates on heme, which is found only in the marrow. To verify that amino alcohol did not quench endogenous fluorescence, the Inventors compared the same region of the bone before and after amino alcohol treatment (FIG. 6).

Quantifying imaging depth at different anatomical regions of the bone (related to FIG. 10): Bone tissue is difficult to clear and image in 3D, particularly in deeper regions where the SNR is low. Additionally, bones are highly heterogeneous and different regions have significantly different biological makeup that affects imaging SNR. In order to characterize the imaging depth capabilities of LSFM in bone tissue cleared by Bone CLARITY, the Inventors quantitatively assessed cell detection in several anatomically distinct regions using a Peak SNR (PSNR) metric (equation 1).

$$PSNR = 20 \times \log_{10} \frac{MAX - \mu}{\sigma} \quad (1)$$

MAX is the maximum intensity of the pixels in the region containing the cell, μ is the mean intensity of all pixels in the region that is at least 20 μm away from the cell center, and σ is their standard deviation. For each anatomical region, the starting point (0 μm) of the sample was defined as the first depth that bone tissue filled at least 50% of the field-of-view. Then, at least 10 isolated Sox9$^+$ cells were selected along the image stack and their PSNR were calculated. For PSNR calculation, an area of 0.123 mm$^2$ and 0.086 mm$^2$ (for long bones and vertebrae, respectively) was used for the region around the cell. Based on visual inspection, the minimum PSNR for cell detection was 24. Consequently, the Inventors could reliably image bone tissue to a depth of approximately 1.5 mm. With the exception of chondrocyte-dense regions such as the growth plate and the epiphysis, this demonstrates that Bone CLARITY and LSFM provide end-to-end imaging of mouse bone tissue. Note that in regions with high concentration of chondrocytes, no isolated cells could be found, thus creating large gaps along the imaging depth in FIG. 10E.

Antibody Staining:

Mice were perfused transcardially with 0.01M PBS followed by 4% paraformaldehyde (PFA). The femurs and tibias were extracted and post-fixed overnight with 4% PFA. The bones were demineralized with 10% EDTA for two weeks at 4 degrees with daily solution exchange. Afterwards, the bones were incubated in 30% sucrose in 0.01M PBS until they sunk. Next, the bones were embedded in OCT compound in a tissue mold cassette and slowly frozen in crushed powder dry ice containing isopentane. The bones were then cut along its longitudinal plane with a cryostat (Leica, Biosystems) until one-half remained. The OCT compound was removed from the bisected bone and cleared following the Bone CLARITY protocol starting with hydrogel embedding and ending before refractive index matching stage. Antibody staining was performed using an anti-osteocalcin antibody from Abcam (ab93876) at 1:100 in 0.5 mM SDS with 0.01% sodium azide for 2 days at room temperature. The bones were then washed for 2 days at room temperature using PBST (0.02% Triton-X 100) and then incubated in secondary conjugated to Alexa-647 for 2 days. Samples were then washed for 2 days and incubated in RIMS stepwise from 1.38-1.47 over 3 days. Bones were then imaged using a Zeiss 780 confocal.

Example 7

Bone CLARITY Renders Intact Bones Transparent while Preserving Endogenous Fluorescence The Inventors developed and applied a bone clearing method to render the tibia, femur, and vertebral column of mice transparent for light microscopy investigation (FIG. 1A). The key steps of the sample preparation, including tissue clearing and autofluorescence removal, are outlined in FIG. 1B and FIG. 5. The bone is decalcified to increase light and molecular penetration through the tissue while leaving a framework of bone matrix with similar structural characteristics to dense fibrous connective tissue. Bone CLARITY uses an acrylamide hydrogel to support the tissue structure and minimize protein loss before the de-lipidation step. The detergent SDS is used to remove lipids to minimize their light-scattering effects. The Inventors observed high autofluorescence in the bone marrow, one of the primary sites of heme synthesis. Because heme is strongly autofluorescent, in the final step of the process, the Inventors used the amino alcohol N,N,N',N'-tetrakis(2-hydroxypropyl) ethylenediamine to remove heme, which minimized marrow autofluorescence by about threefold (FIG. 6). All of the above clearing stages were conducted on a temperature-controlled stir plate that provided continuous convective flow (FIG. 7; auxiliary design file). This accelerates and improves the clearing process for entire organs compared with passive clearing. Notably, the samples did not change size during the clearing process (FIG. 8).

The imaging of intact bone tissue using a point-scanning method (such as a confocal microscope) poses an operational challenge because acquisition times are prolonged, with concomitant photobleaching. To address this, the Inventors built a custom light-sheet fluorescence microscope (LSFM) with confocal slit detection (FIG. 9). To modify the LSFM to image bones, the Inventors added an additional light-sheet path to illuminate the bones from two opposite directions. This additional light path improved optical access to areas containing a high percentage of cancellous bone, which typically scatter light more extensively and consequently lower the SNR. Given a particular depth scan, the sample is illuminated by only one of the two light-sheet paths, whichever provides the better contrast. The Inventors use only one illumination path per depth scan because there is always one illumination direction that scatters less light and thus provides superior image quality. To minimize RI mismatch between the objective lens and the bones, the Inventors directly immersed the samples in the immersion chamber without the use of a quartz cuvette to hold the sample. If RI variations still persist, the position of the detection objective is changed for each tile and specific depth along the Z-scan, to mitigate any resulting out-of-focus aberrations. The LSFM captures images at a frame rate of 22 frames per second (16-bit depth) and produces 0.176 gigabytes (GB) of imaging data per second. Large data sets are thus acquired for each imaged bone (50 to 500 GB). To manage these large data sets, the Inventors designed a computational pipeline that includes image stitching, automatic detection of individual cells, and volume-of-interest (VOI) rendering for analysis (FIG. 1C).

To validate the protocol, the Inventors applied the Inventors' clearing and imaging method to locate progenitor cells in the long bones and vertebrae of transgenic reporter mice. A Sox9CreER transgenic mouse line was used in which, upon tamoxifen injection, multipotent osteoblast and chondrocyte progenitor cells express tdTomato. The Inventors visualized the endogenous fluorescence of Sox9+ cells using Bone CLARITY (FIGS. 1, D and E). Quantification of the imaging depth in different regions of the tibia, femur, and vertebral body showed that the Inventors were able to image through the diaphysis of the femur and tibia and the entire vertebral body. Furthermore, the Inventors were able to reliably detect Sox9$^+$ cells up to about 1.5 mm deep into the bones (FIG. 10). Collectively, Bone CLARITY coupled with LSFM and the data processing pipeline is an effective clearing, imaging, and data processing protocol for investigating intact mouse bones.

Example 8

Figures 2, 2A:
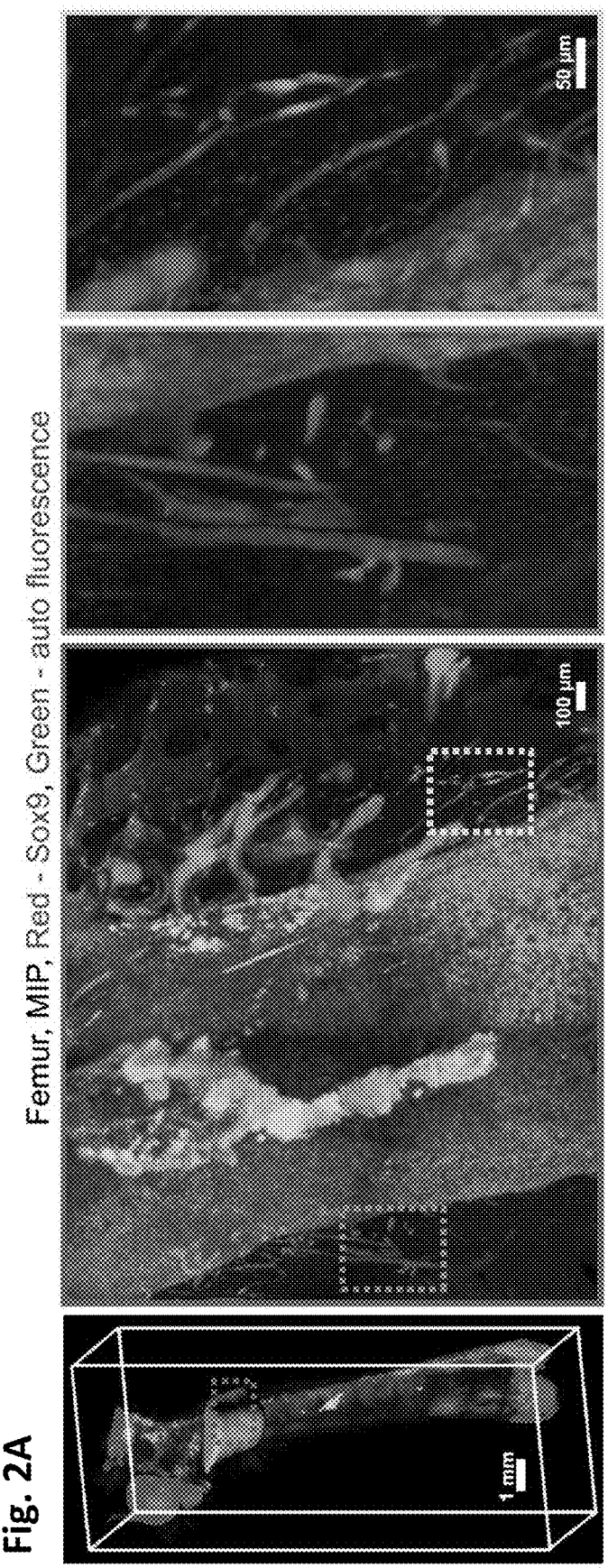
FIG. 2. Bone (Clear Lipid-exchanged Acrylamide-hybridized Rigid Imaging/Immunostaining/In situ hybridization-compatible Tissue hYdrogel) CLARITY enables quantification of fluorescently labeled $Sox9^+$ cells in the mouse tibia and femur.
(FIG. 2A) Femur MIP fluorescence image and magnified images showing single $Sox9^+$ cells in the vicinity of the third trochanter (red, Sox9; and green, autofluorescence). The gray surface surrounding the femur represents an overlay of the VOI; only the cells that reside within the VOI are quantified. The purple, blue, and yellow boxed regions in the MIP represent progressive magnification.
Figures 11, 11A:
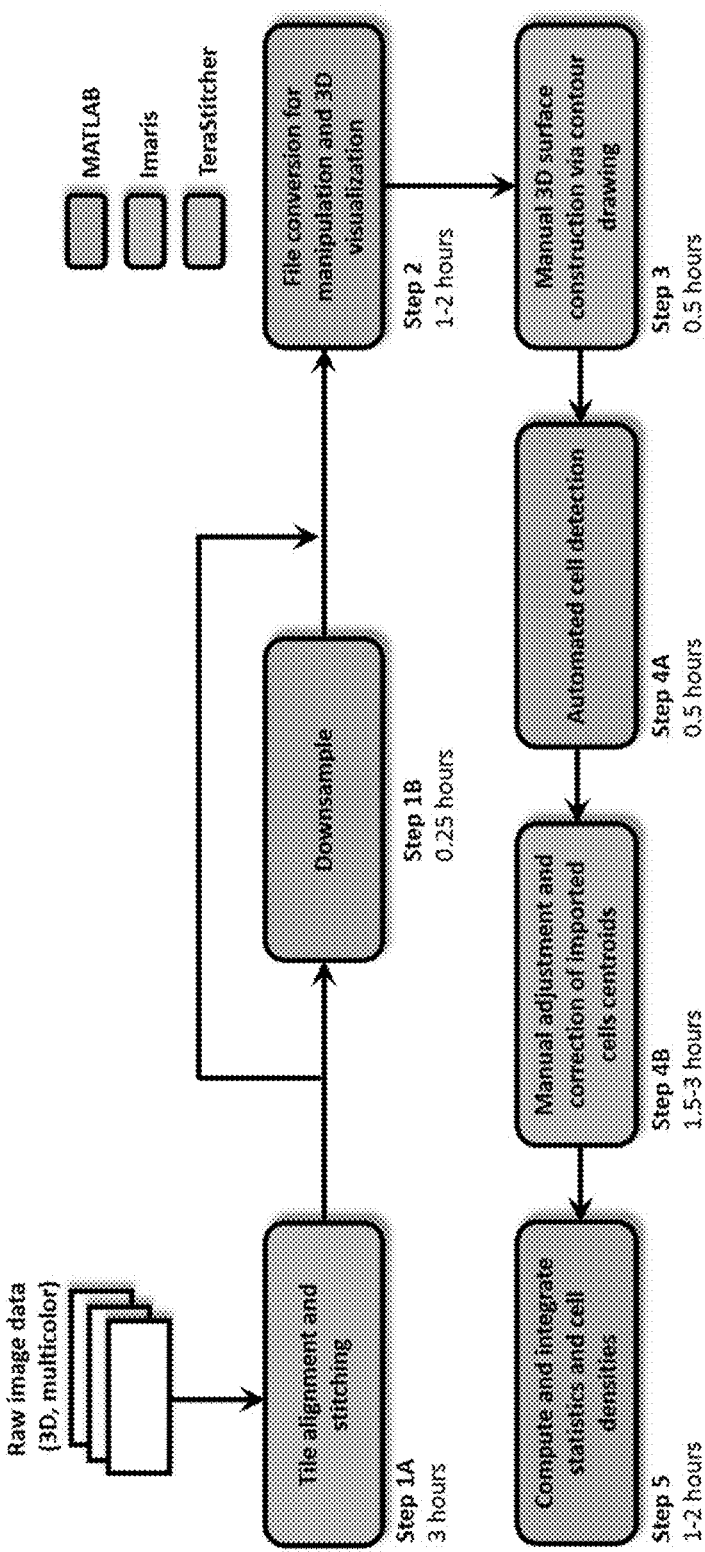
FIG. 11. Computational pipeline.
(FIG. 11A) A block diagram of the computational pipeline.
Figure 11:
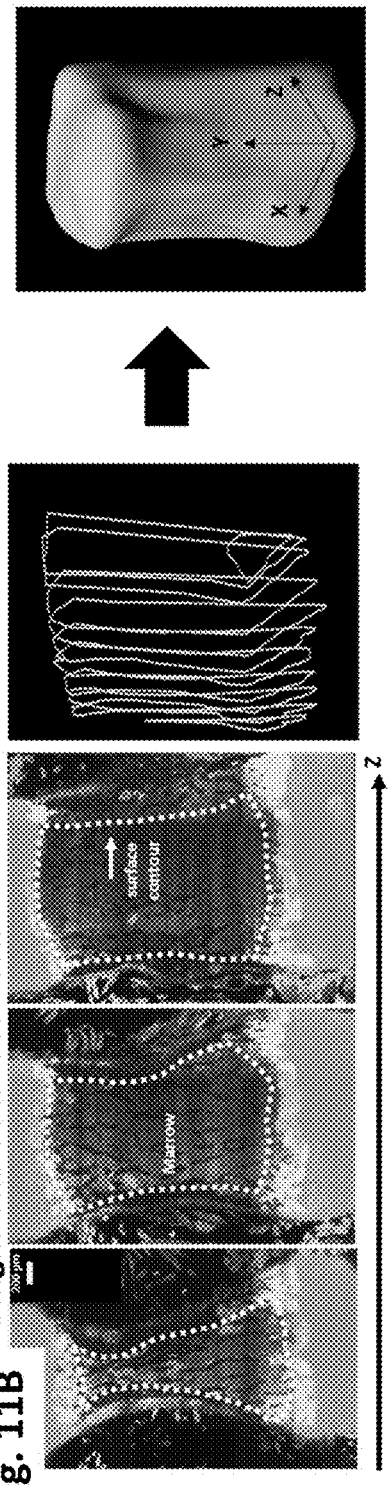
Figure 11B:
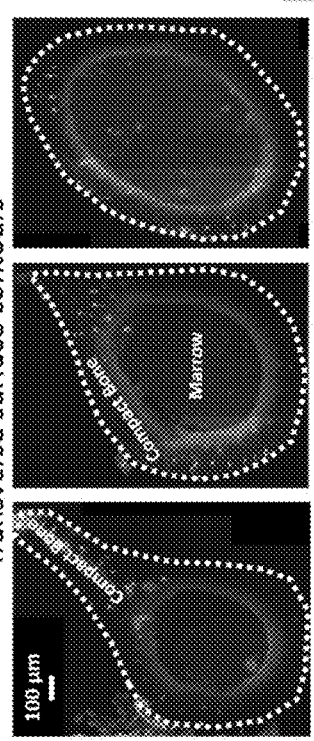
(FIG. 11B) Volume of interest (VOI) creation in the vertebra body. In each block of approximately 10 longitudinal sections a region of interest (ROI) (dotted line) is marked around regions that contain marrow. The VOI is then interpolated from the ROIs.
Figure 11C:
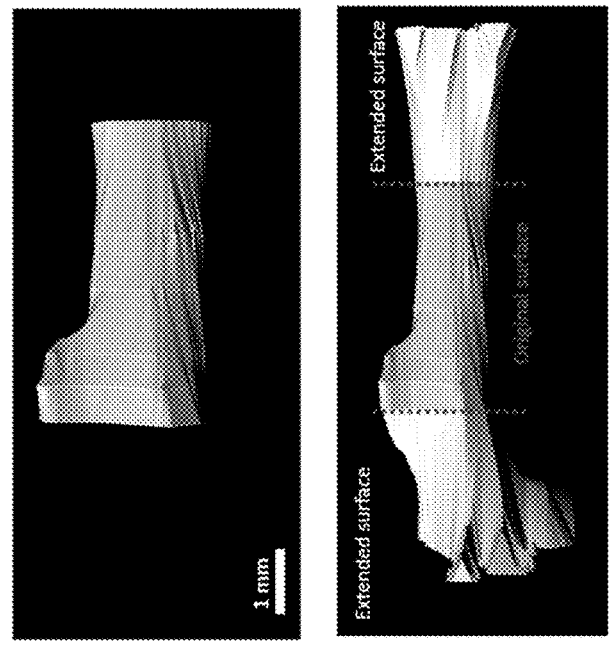
(FIG. 11C) VOI creation in the tibia and femur, where approximately 10 transverse slices are used to create the VOI. For cell distance to surface calculation, the VOI is extended from both ends, in order to ensure distance calculation to the real bone boundaries and not to artificial perpendicular surfaces.

Semiautomated Computational Pipeline Quantifies Sox9$^+$ Cells in Mouse Tibia and Femur To demonstrate that biological environments can be observed and quantified with Bone CLARITY, the Inventors first counted Sox9 cells in the tibia and femur. The Inventors found that Bone CLARITY allows for detection and quantification of individual Sox9$^+$ cells in 3D (FIG. 2A), some of which appear associated with small blood vessels. Owing to the large VOI (FIG. 2A; gray surface), the Inventors created a semiautomated cell detection algorithm (FIG. 2B and FIG. 11). The algorithm divides the 2D images that make up the Z-stack (or depth scan) into n small overlapping regions, and then adaptively thresholds the 2D images into binary images on the basis of the local mean and SD of fluorescence. The resulting binary 2D images are further subjected to morphological operations to eliminate noise and discontinuity within a cell. All of the 2D binary images are then combined into a 3D matrix. From the 3D matrix, only volumes that fit the properties of a Sox9+ cell are maintained, thus avoiding erroneous counting of large blood vessels or small autofluorescence artifacts. All cells outside the user-defined VOI (FIG. 2A) are discarded. The cell candidate centroid locations are then imported to 3D visualization software for manual quality control. During the quality control stage, the annotator reviews the entire 3D volume and corrects the automatic results by marking false-negative cells and omitting false-positive cells. Therefore, at the end of the quality control stage, the cell counts are equivalent to cell counts that were performed manually. According to the Inventors' experiments, a fully automatic pipeline only achieves 52% sensitivity and 36% precision on average. Note that removing false positives is a faster operation in the 3D visualization software than adding false negatives; therefore, the value of sensitivity outweighs the need for precision.

Figure 12:
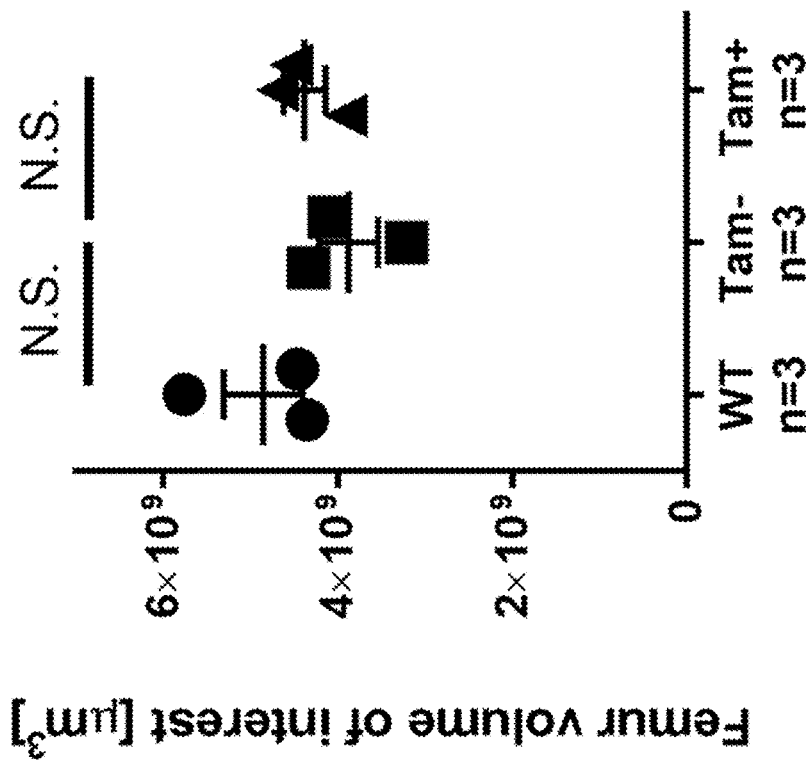
FIG. 12. Volume comparisons in the tibia and femur. No significant change in the volume of interest was observed between the $Sox9^+$ and $Tam^+$ group and the two control groups (wild type; $Sox9^+$ and $Tam^-$). All values are mean±s.e.m; two-tailed, unpaired t-test, ($p \geq 0.05$=n.s.).
Figure 12:
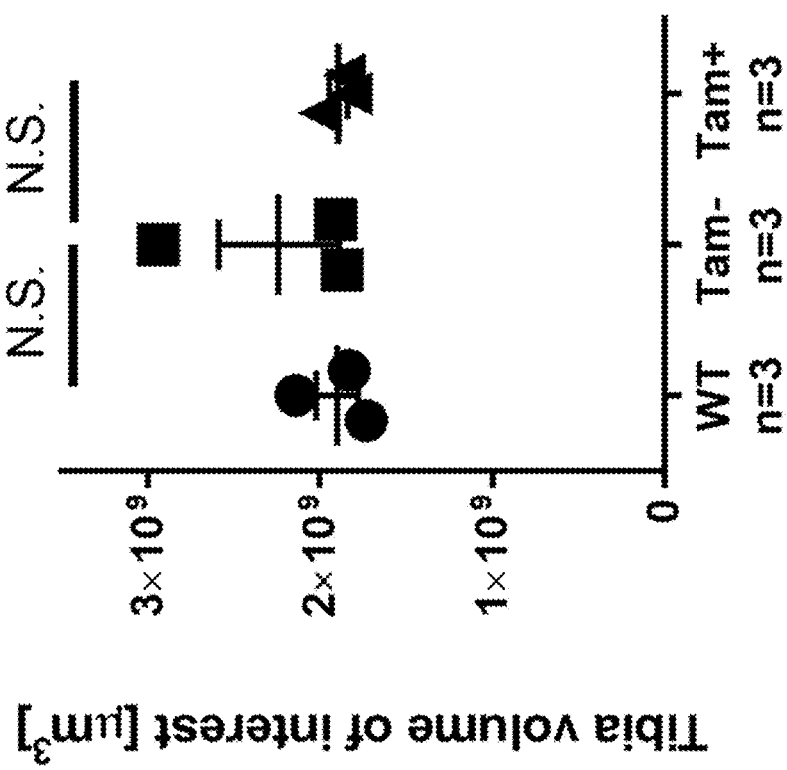
Figure 13:
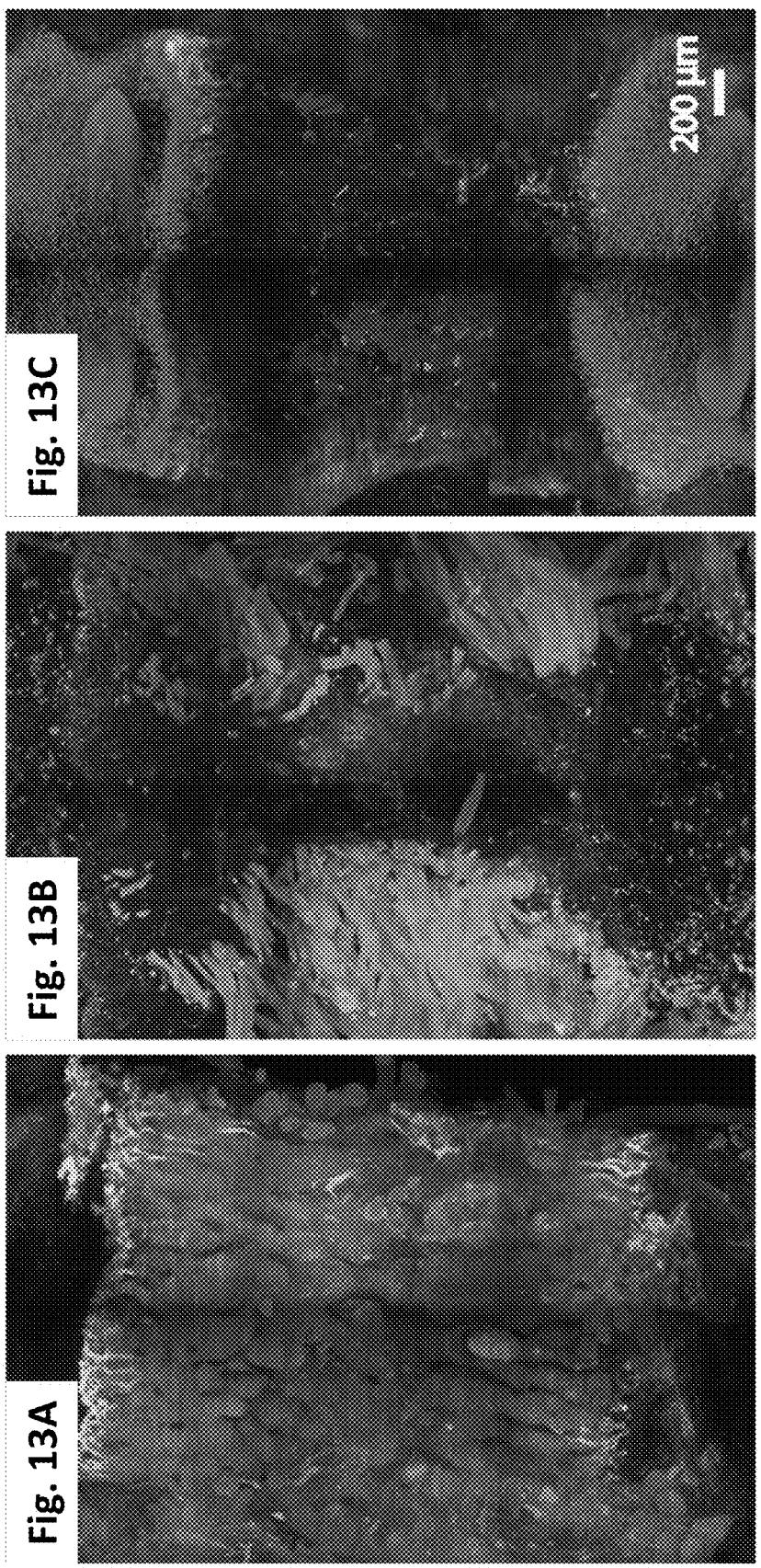
FIG. 13. TdTomato expression in the vertebra columns.
Figure 14:
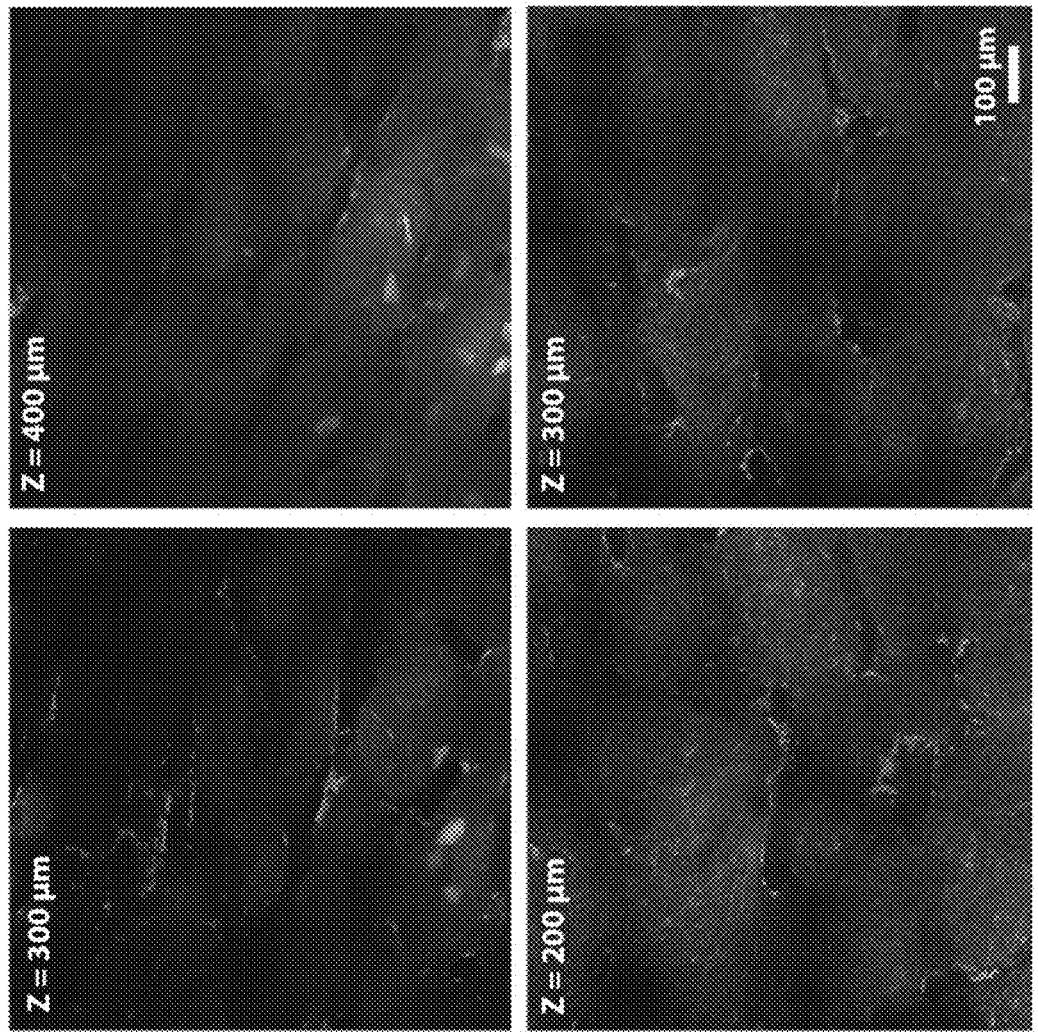
FIG. 14. Antibody staining using Bone CLARITY.
Figure 14A:
(FIG. 14A) The approximate region imaged in the bisected femur is outlined by a black square. Digital slices of 10 µm thickness are shown in 300 and 400 µm from the surface of the femur. Red shows Osteocalcin staining of cells lining the surface of bone, green shows auto-fluorescence.
Figure 14B:
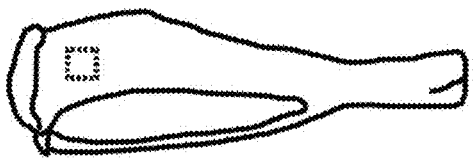
(FIG. 14B) The region imaged in the bisected tibia is outlined by a black square. Digital slices of 10 µm thickness are shown in 200 and 300 µm from the surface of the tibia. Red shows Osteocalcin staining of cells lining the surface of bone, green shows auto-fluorescence.

The Inventors quantified the number of fluorescently labeled Sox9+ cells in the femur and tibia of Sox9CreER mice versus two control groups: Sox9CreER mice without tamoxifen administration and wild-type mice without the transgenes (FIG. 2C). The analyzed volume for each group was comparable (FIG. 12). The cell counts in the Sox9CreER group without tamoxifen administration can be attributed to leakage of the reporter line because there was no visible expression of tdTomato in the wild-type control samples. Qualitatively, this expression leakage can be observed in FIG. 13, where the expression of the tdTomato signal is compared between the experimental group and the two control groups. The Inventors next quantified the cell distribution as a function of distance from the periosteal surface along the longitudinal plane (schematic in FIG. 2D). On the basis of the Inventors' analysis, most of the cells in the diaphysis reside adjacent to the endocortical surface, with mean distances from the periosteal surface of about 136.9 and 143.6 mm for the tibia and femur, respectively (FIG. 2E). This result supports similar findings in and validates Bone CLARITY as a reliable method to resolve and quantify individual cells in intact bone and marrow spaces. Note that Bone CLARITY is not limited to visualizing cell populations in trans-genic animals only and that antibody staining is also feasible (FIG. 14). However, for maximum penetration of the antibody into the bone for secondary staining, it is recommended to bisect the bone before the clearing process.

Example 9

Bone Clearing can Complement Section-Based Stereology

Design-based stereology is the gold standard method to quantify total cell numbers and densities in organs while preserving spatial information. Stereology relies on statistical sampling methods. Systematic uniform random sampling (SURS) is a frequently used sampling method that efficiently reduces the variance of the estimate compared with random sampling. SURS obtains histological sections from an organ to reduce the amount of tissue for analysis. SURS samples at regular uniform intervals with the first sample collected at a random position within the first interval. The number of cells in a tissue volume is a OD geometric feature. Thus, to avoid bias due to cell size or shape, a probe based on two thin physical sections or optical planes separated by a known distance (dissector) is used to accomplish quantification. Cells are typically counted in a known fraction of the organ, which allows for an estimation of the total number of cells in the entire organ. The spatial distribution of cells can also be obtained using second-order stereological methods.

Applying stereological methods to cleared organs offers notable time-saving because clearing precludes the need for labor-intensive sectioning. Using the Bone CLARITY method and the Inventors' 3D counting scheme, the Inventors investigated the variability in stereology estimates as a function of the number of slices for both SURS and simple random sampling in stereology experiment simulations. FIG. 3A shows one representative selection of n random uniformly spaced sections for a simulated SURS experiment in the femur, tibia, and vertebral body. FIG. 3B shows the estimates for the cell count of an entire VOI based on n sampled slices, and FIG. 3C shows the coefficient of variation of simulated stereology experiments that were conducted with n slices. To estimate the coefficient of variation for each n representative slices, the Inventors conducted five simulated stereology experiments. As expected in these simulations, variance decreased rapidly with increasing number of slices for femur, tibia, and vertebra. Precision of the stereological estimate would likely be improved with proportionator sampling, a form of nonuniform sampling better suited to rare structures. Nonetheless, the 3D counting method offers several advantages for quantifying rare cellular populations: the ability to detect subtle changes that might be overlooked because of sampling variance, elimination of the need for sectioning, and 3D visualization.

Example 10

Scl-Ab Increases the Number of Sox9$^+$ Cells in the Vertebral Column

The Inventors next applied Bone CLARITY to the vertebral column, a bone that is highly susceptible to fractures due to osteoporosis and whose complex geometry is particularly difficult to probe with traditional sectioning-based methods. The Inventors cleared and imaged the vertebrae from mice and focused on the fourth lumbar vertebral body (L4), which is dense, opaque, and predominately composed of cancellous bone. FIGS. 4 (A and B) shows schematics of lateral and transverse cuts from a representative vertebra. FIG. 4B also shows the approximate locations (dashed lines) of the digital sections (30 mm thick) that are shown in FIG. 4C. The lateral processes that extrude from the vertebral body can be seen in the horizontal edges of the 650-mm section. These processes were excluded from the cell counts, as illustrated by the representative VOI (FIG. 4D). In addition, careful attention was given to ensure the exclusion of the intervertebral discs and cartilage endplates from the VOI because they are both primarily populated by chondrocytes. These chondrocytes express Sox9 and are tdTomato+ after tamoxifen administration and thus require careful exclusion for accurate cell counts of fluorescently marked osteopro-genitors. The quantification of vertebral Sox9-tdTomato cells after tamoxifen administration versus the two control groups, Sox9CreER mice without tamoxifen administration and wild-type mice, can be seen in FIG. 4E. Again, the Inventors observed that the Sox9CreER transgenic animals without tamoxifen administration display mild leakage of tdTomato expression (FIG. 4E and FIG. 13). Overall, similar to the cell distribution results presented for the tibia and femur, the Sox9+ cells were primarily located adjacent to the endocortical surface (FIGS. 4, F and G), with a mean distance of 138.8 and 137.6 mm for the Tam− and Tam+ groups, respectively.

The Inventors next tested the effects of Scl-Ab on the total number of Sox9+ cells in the vertebral column. Sclerostin is an extracellular inhibitor of the canonical Wnt signaling pathway and is highly expressed in osteo-cytes. Inhibition of sclerostin leads to activation of canonical Wnt signaling in the osteoblast lineage, resulting in a rapid but transient marked increase in osteoblast number and corresponding bone formation. Although the early marked increase in osteoblast number is considered to be at least in part due to activation of bone lining cells, the contribution of osteoprogenitors to this early increase in osteoblast number is unclear. Although a decrease in osteoprogenitors has been demonstrated to be associated with the attenuation of bone formation that occurs with long-term Scl-Ab treatment in rats, stereological methods have not detected effects on progenitor number coincident with the maximal increase in osteoblast number. To gain insight into the acute effects of Scl-Ab on osteoprogenitors, the Inventors conducted an experiment as outlined in FIG. 4H. On day 1, Sox9CreER mice the were injected with Scl-Ab (100 mg/kg subcutaneously). Four days after, the Inventors provided a second dose of Scl-Ab along with tamoxifen to label Sox9+ cells with tdTomato. The Inventors euthanized the animals 5 days later and cleared the bones using Bone CLARITY. After performing blinded quantification of Sox9+ cells, the Inventors observed an increase in the total number of Sox9+ cells in the vertebral body 9 days after initial Scl-Ab treatment versus the vehicle control group (FIG. 4I). The Inventors did not observe any significant changes to the vertebral body volume (FIG. 4J) between the experimental and control groups at this early time point. These results demonstrate that there is an increase in osteoprogenitors that are likely recruited to the bone surface to contribute to the increase in osteoblast number. The distribution of cells as a function of distance from the surface can be seen in FIG. 4K, with mean distances of about 99.9 and 137.8 mm for the vehicle and treated groups, respectively.

Example 11

Discussion

In the bone remodeling process, bone health is maintained through continuous cycles of bone resorption by osteoclasts and bone formation by osteoblasts. Imbalances in these physiological processes can lead to various bone diseases, such as osteoporosis, which affect millions of people in the United States alone. To gain better insight into potentially effective treatments for osteoporosis, it is imperative to study the physiological processes that occur in healthy and diseased bone and understand its molecular and cellular mechanisms within the 3D microenvironment. The Inventors demonstrate that the Bone CLARITY technique renders the tibias, femurs, and vertebral bodies of mice optically transparent while preserving bone morphology and an endogenous fluorescent reporter signal. In addition to matching the RI of the tissue, Bone CLARITY also removes minerals and lipids, thus enabling the Inventors to reconstruct a whole vertebral body and the entire diaphysis from the tibia and femur.

For maximum impact, clearing and imaging platforms need to be easy to use and scalable. The trio of methods presented here has a few limitations in its current rendering that could be improved in the future, such as the addition of antibody staining to the clearing workflow, reducing processing time, and overcoming the technical barriers of acquiring and analyzing big data sets. Antibody staining of an intact bone is challenging because of poor penetration by relatively large antibodies. To improve antibody penetration, the Inventors bisected and cleared half of a tibia and femur. In the bisected and cleared bones, the antibody penetrated up to 400 mm from the bone surface and showed high specificity and SNR (FIG. 14). The use of small-molecule staining methods [for example, single-molecule hybridization chain reaction] could allow the labeling of intact bones while achieving improved staining depths. Meanwhile, the ability to retain and detect endogenous fluorescence has proven highly enabling, although the gentle clearing reagents used in Bone CLARITY do introduce a compromise in processing time (28 days). Using faster decalcification agents, such as formic acid, might shorten the current deCAL time of 14 days, although the fluorescent proteins generated by the reporter genes used in this study might lose their fluorescence under acidic conditions. Delipidation is also a lengthy stage in Bone CLARITY but necessary to reduce scattering from lipids not only present in the mineralized bone tissue but also highly abundant within the bone marrow. Consequently, delipidation ensures high-quality optical access deep in the bone. Although the use of customized microscopy and software might not be easy to implement in a nontechnical setting, commercial LSFM systems with a streamlined user interface and associated software are rapidly evolving to support the types of applications described here. For data processing, the Inventors found that fully automated cell detection algorithms were difficult to apply within cleared tissue. SNR variations arising from nonuniform illumination and fluorescence detection within the bone resulted in unsatisfactory precision, necessitating manual quality control. The simple automated tools that the Inventors developed are fast and adaptive and, in general, are able to save annotator time while improving precision and reducing error; however, more work is required to achieve a reliable, fully automated algorithm for cell counting. In general, data handling, visualization, and analysis would benefit from individual developers sharing their code in an open-source environment, which would allow the scientific and medical community to efficiently customize software relevant for the application at hand.

Bone CLARITY enables clearing of mouse bones while retaining the integrity of the bone marrow and endogenous fluorescence. After clearing, the Inventors achieved 3D reconstructions of a vertebral body and long bone diaphyses and attained an imaging depth of about 1.5 mm for the epiphysis of long bones. Using a computational pipeline to process large data sets and detect single cells in bone, the Inventors mapped the spatial distribution of osteoprogenitor cells. In addition, the Inventors demonstrated the advantages of 3D methods in estimating rare cell populations that are not readily amenable to sampling by traditional stereology methods. Note that combining traditional stereology methods with tissue clearing techniques can be advantageous, especially in cases where quantification of complicated structural elements cannot be done automatically. Therefore, subsampling is advantageous for manual quantification within a reasonable time frame. Last, to further demonstrate the use of the Inventors' clearing method, the Inventors treated a cohort of adult reporter mice with Scl-Ab, a bone-forming agent, for 9 days. Previous stereological studies in rats treated with Scl-Ab for 8 days revealed a marked increase in total osteoblast number in the vertebrae coincident with increased bone formation but no significant effect on bone progenitor numbers. After 9 days of treatment in mice, the Inventors found that the total number of osteoblast progenitor cells increased by 36% compared with the control group. This result was not surprising based on the literature, but it has been challenging to demonstrate using stereological methods given the rarity of osteoprogenitor cells, particularly in the vertebrae. This underscores the greater sensitivity of the Inventors' clearing, imaging, and data-processing protocol for quantifying rare cell populations and using lineage tracing to mark progenitors, as opposed to immunophenotyping in tissue sections. Overall, continued developments in tissue clearing, imaging, and data analysis can facilitate translational research that will provide insight into the efficacy and safety of new bone-modulating drugs by profiling their effects on progenitor cell populations.

Other fields might also benefit from applying the bone clearing technique, such as neuroscience. Removal of the skull damages the interface between the skull and the underlying vascular bed and neuronal tissue. Preservation of this interface would be beneficial for studying the lymphatic vessels residing within it, assessing head trauma (for example, percussive injuries), and characterizing the positioning of head-mounted brain implants in an intact environment.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are techniques and compositions for cleared bone tissue samples, visualize cleared bone tissue samples, quantifying and detecting elements within cleared bone tissue samples, and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. A method, comprising:
   fixing a bone tissue sample by applying a fixative solution to generate a fixed bone tissue sample;
   decalcifying the fixed bone tissue sample by applying a decalcifying solution comprising a calcium chelating agent to generate a decalcified bone tissue sample;

stabilizing the decalcified bone tissue sample by applying a hydrogel monomer solution;
initiating polymerization of the monomer solution to generate a decalcified bone tissue sample hydrogel matrix;
washing the decalcified bone tissue sample hydrogel matrix;
removing lipids from the washed decalcified bone tissue sample hydrogel matrix by applying a detergent solution to generate a substantially cleared bone tissue sample;
removing heme from the substantially cleared bone tissue sample by applying a removal solution comprising an amino alcohol to generate a cleared bone tissue sample;
further washing the cleared bone tissue sample;
serially applying refractive index matching solutions (RIMS) with progressively higher refractive indexes (RIs) to the cleared bone tissue sample; and
using a microscope to visualize the tissue comprising the bone tissue sample comprising bone and bone marrow of the subject that has been incubated in the final RIMS at an imaging depth below 200 mm.

2. The method of claim 1, wherein the fixative solution comprises 2-6% paraformaldehyde (PFA).

3. The method of claim 2, wherein the fixative solution comprises 4% PFA.

4. The method of claim 1, wherein the calcium chelating agent comprises ethylenediaminetetraacetic acid (EDTA).

5. The method of claim 1, wherein the hydrogel monomer solution comprises 2-8% acrylamide.

6. The method of claim 5, wherein the hydrogel monomer solution comprises 4% acrylamide.

7. The method of claim 1, further comprising
placing the decalcified bone tissue sample into a substantially air tight chamber, and introducing nitrogen into the substantially air tight chamber.

8. The method of claim 1, wherein the hydrogel monomer solution comprises a thermoinitiator or photoinitiator.

9. The method of claim 1, wherein the detergent solution comprises 6-15% sodium dodecyl sulfate (SDS).

10. The method of claim 9, wherein the detergent solution comprises 8% SDS.

11. The method of claim 1, wherein the removal solution comprising the amino alcohol comprises N,N,N',N'-Tetrakis(2-Hydroxypropyl)ethylenediamine.

12. The method of claim 11, wherein the removal solution comprises 25% N,N,N',N'-Tetrakis(2-Hydroxypropyl)ethylenediamine.

13. The method of claim 1, wherein a first RIMS in which the tissue comprising the bone of the subject is incubated has an RI of 1.36-1.40.

14. The method of claim 13, wherein a second RIMS in which the tissue comprising bone is incubated has an RI of 1.41-1.45.

15. The method of claim 14, wherein the tissue comprising bone is incubated in a third RIMS that has an RI of 1.45-1.47.

16. The method of claim 1, wherein stirring, flow assistance or constant flow is introduced for one or more steps of: applying a decalcifying solution, applying a hydrogel monomer solution, washing the decalcified bone tissue sample hydrogel matrix, applying a detergent solution to generate a substantially cleared bone tissue sample, applying a removal solution, and further washing the cleared bone tissue sample.

17. The method of claim 1, wherein the microscope is a light sheet microscope.

18. A method comprising:
fixing a bone tissue sample by applying a fixative solution comprising 4% paraformaldehyde (PFA) to generate a fixed bone tissue sample;
decalcifying a fixed bone tissue sample by applying a decalcifying solution comprising ethylenediaminetetraacetic acid (EDTA) and stirring to generate a decalcified bone tissue sample;
stabilizing the decalcified bone tissue sample by applying a hydrogel monomer solution comprising 4% acrylamide with flow assistance;
initiating polymerization of the monomer solution to generate a decalcified bone tissue sample hydrogel matrix;
washing the decalcified bone tissue sample hydrogel matrix with flow assistance;
removing lipids from the washed decalcified bone tissue sample hydrogel matrix by applying a detergent solution comprising 8% sodium dodecyl sulfate (SDS) with flow assistance to generate a substantially cleared bone tissue sample;
removing heme from the substantially cleared bone tissue sample by applying a removal solution comprising 25% N,N,N',N'-Tetrakis(2-Hydroxypropyl)ethylenediamine with flow assistance to generate a cleared bone tissue sample;
further washing the cleared bone tissue sample with constant stirring;
serially applying refractive index matching solutions (RIMS) with progressively higher refractive indexes (RIs) to the cleared bone tissue sample; and
using a microscope to visualize the bone tissue sample comprising bone and bone marrow of the subject that has been incubated in the final RIMS at an imaging depth below 200 mm.

19. The method of claim 1, wherein the imaging depth is below 100 mm.

20. The method of claim 18, wherein the imaging depth is below 100 mm.

* * * * *